United States Patent [19]

Mushabac

[11] Patent Number: 5,224,049
[45] Date of Patent: Jun. 29, 1993

[54] METHOD, SYSTEM AND MOLD ASSEMBLY FOR USE IN PREPARING A DENTAL PROSTHESIS

[76] Inventor: David R. Mushabac, 919 Ocean Ave., Brooklyn, N.Y. 11226

[21] Appl. No.: 526,512

[22] Filed: May 21, 1990

Related U.S. Application Data

[63] Continuation-in-part of Ser. No. 503,162, Apr. 10, 1990.

[51] Int. Cl.⁵ ............... G06F 15/42; G06F 15/46; G06F 15/60
[52] U.S. Cl. ............... 364/474.05; 264/222; 425/2; 425/135; 433/34; 433/223; 364/413.28; 364/474.24
[58] Field of Search ............ 364/413.28, 468, 474.05, 364/474.24, 473, 476; 264/16–20, 40.5, 138, 219, 220, 222, 227, 328.1, 328.8; 425/2, DIG. 11, 135, 142, 150, 519–521, 116; 433/34–48, 56, 73, 204, 213, 223; 128/776, 777; 33/513, 514; 249/54

[56] References Cited

U.S. PATENT DOCUMENTS

| | | | |
|---|---|---|---|
| 3,971,133 | 7/1976 | Mushabac | 433/213 |
| 4,149,246 | 4/1979 | Goldman | 364/470 X |
| 4,182,312 | 1/1980 | Mushabac | 433/68 |
| 4,239,431 | 12/1980 | Davini | 414/730 |
| 4,349,277 | 9/1982 | Mundy et al. | 356/376 |
| 4,431,420 | 2/1984 | Adair | 433/199 |
| 4,436,684 | 3/1984 | White | 264/16 |
| 4,525,858 | 6/1985 | Cline et al. | 382/1 |
| 4,564,295 | 1/1986 | Halioua | 356/376 |
| 4,575,805 | 3/1986 | Moermann et al. | 364/413.28 |
| 4,577,968 | 3/1986 | Makosch | 356/356 |
| 4,598,376 | 7/1986 | Burton et al. | 364/470 |
| 4,611,288 | 9/1986 | Duret et al. | 364/413.28 X |
| 4,657,394 | 4/1987 | Halioua | 356/376 |
| 4,663,720 | 5/1987 | Duret et al. | 364/413.28 X |
| 4,837,732 | 6/1989 | Brandestini et al. | 364/413.28 |
| 4,936,862 | 6/1990 | Walker et al. | 364/468 X |
| 4,941,826 | 7/1990 | Loran et al. | 433/76 X |
| 5,027,281 | 6/1991 | Rekow et al. | 364/474.24 |

OTHER PUBLICATIONS

"Optical Methods to Measure Shape and Size", P. M. Boone *Adv. Dent. Res.* 1(1):27–38, Oct. 1987.

*Primary Examiner*—Joseph Ruggiero
*Attorney, Agent, or Firm*—R. Neil Sudol; Henry D. Coleman

[57] ABSTRACT

A method for use in preparing a dental prosthesis comprises the step of receiving an electrical signal encoding geometric specifications of a substructure of the prosthesis, the specifications including dimensions and shape of a tooth preparation at a dental site at which the prosthesis is to be affixed and the configuration of the substructure. In a subsequent step performed in response to the electrical signal, a computer is operated to automatically select a first mold component having a surface corresponding in dimensions to the tooth preparation and to automatically select a second mold component to produce, in cooperation with the first mold component, a mold cavity having dimensions and configuration corresponding to dimensions and configuration of the substructure. The first mold component and the second mold component are placed in predetermined relative positions to form the mold cavity and the mold cavity is filled with a quantity of a fluidic solidifiable dental material, i.e., a precious metal, semi-precious metal, alloy or other usable dental material.

60 Claims, 14 Drawing Sheets

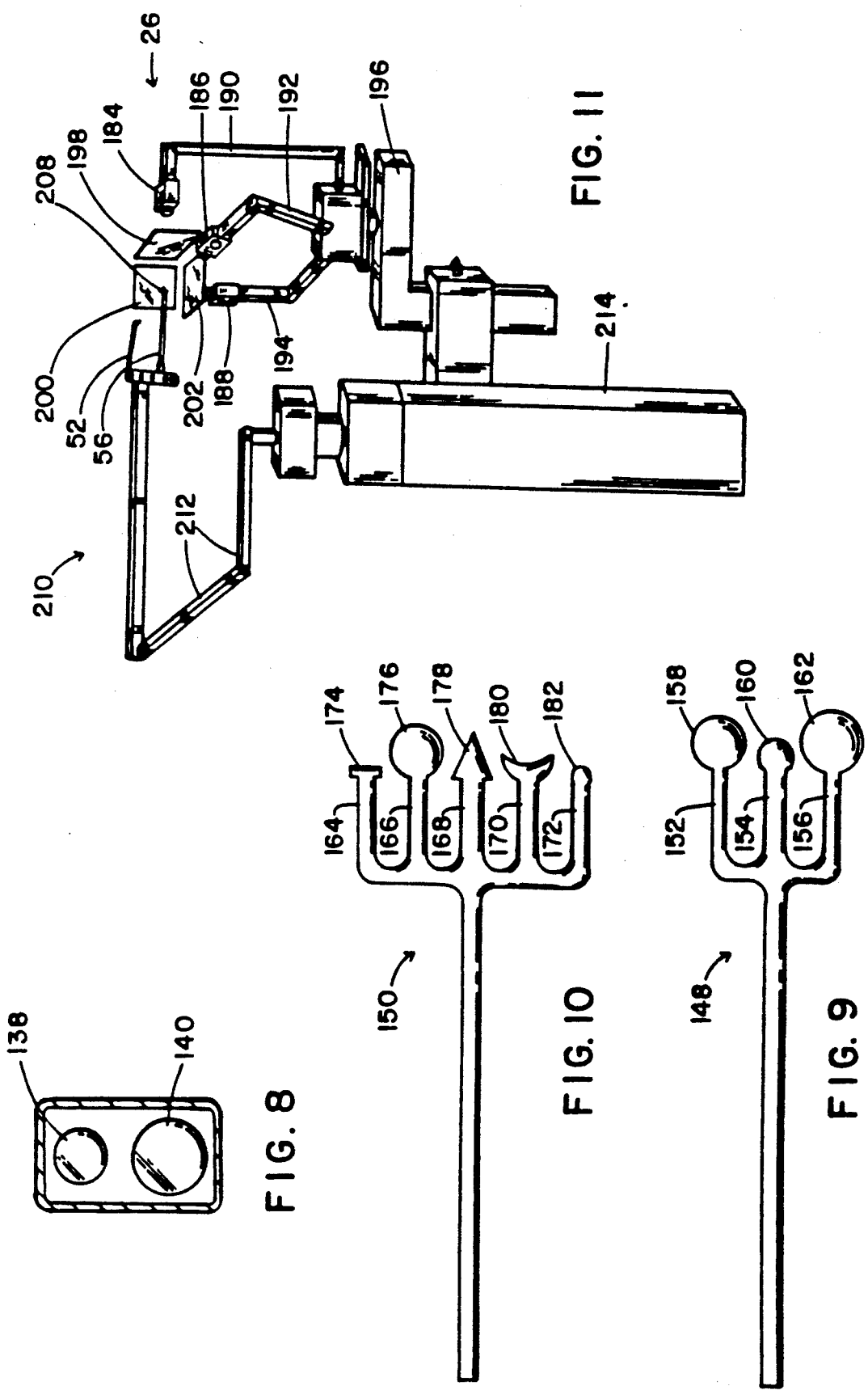

METHOD, SYSTEM AND MOLD ASSEMBLY FOR USE IN PREPARING A DENTAL PROSTHESIS

CROSS-REFERENCE TO A RELATED APPLICATION

This application is a continuation-in-part of application Ser. No. 507,162 filed Apr. 10, 1990.

BACKGROUND OF THE INVENTION

This invention relates to method for preparing a dental prosthesis. This invention also relates to an apparatus or system for use in carrying out the method. In addition, this invention relates to a mold assembly for preparing a dental prosthesis. More particularly, this invention relates to a method, an associated apparatus or system and a mold assembly for manufacturing substructures, particularly metal or alloy copings, of prosthetic dental overlays such as crowns, bridges and splints.

In accordance with conventional techniques for providing a dental patient with a prosthetic overlay such as a crown, bridge or splint, a dental practitioner grinds the subject tooth or teeth down to form one or more tooth preparations to which the prosthetic device is to be attached. An impression of the tooth preparation or tooth preparations is taken in an elastic material and the impression is used to produce a model with dies. This in turn has a wax shape built to fit the die, so that a metal casting can be processed via the lost wax technique. The metal casting is then provided with a porcelain layer.

This method of casting for manufacturing prosthetic dental devices is labor intensive and, accordingly, expensive. In addition, the time required to make a dental prosthesis by such labor intensive methods is substantial and thus results in considerable delay in providing patients with crowns, bridges and splints.

The metal castings for the prosthetic devices are generally made by dental laboratories from metals or alloys purchased in the form of small ingots. After applying porcelain cover layers to the metal castings, the laboratories ship the finished prothetic products to the dental practitioners who ordered them.

The manufacture of customized dental prostheses entails substantial efforts and time expenditures by dental laboratories to customize the fit of the castings, resulting in a reduction in value of the precious metal and a using of amounts of precious metals in the process that is lost in castings, grindings. The casting system is subject to so many variables as waxing thicknesses, investment expansions, metal homogenities that there are necessarily inaccuracies and errors in castings results, increased expense in the delivery of what is required and delay in the finalized, correctly fitted prosthetic dental devices. In addition, it is frequently necessary for the dental technicians to hand shape required margins as well as eliminate small bubbles from the metal castings and to grind both internal and external surfaces of the prosthetic appliance in preparation for use and insertion in in the patients, mouths. This grinding away of expensive precious metal or any other metals is time consuming and results in inaccuracies, modifications of fit, amd higher costs for precious metals.

In producing bridges or splints pursuant to traditional methods, the bridges or splints are frequently fabricated by using the excess materials of several prior castings, these prior castings being the excess of the sprued units. This manufacturing technique, as discussed above, is labor intensive and therefore results in high costs. In addition, in cases where there are soldered joints in a prosthetic dental device there is an unequal distribution of stress responsive forces throughout the device, and as a consequence multi-unit cases may be subject to failure due to porosity and/or fatigue at the soldered joints. Moreover, gases are generated in the casting and/or soldering process and such gases remain in the metal and are released and weaken the procelain when that material is baked onto the metal.

Because handheld grinding and/or drilling of the metal castings naturally results in reduced accuracies in the shapes of the final products and because conventional techniques for manufacturing dental prostheses such as crowns, bridges and splints are subject to continuous variables from the impression stage, to the modeling, waxing, casting and handheld grinding, a goodly number of dental prostheses are frequently ill-fitting or require multiple corrective steps, which gives rise to further variables, delays and cost increases.

New methodologies based on CAD/CAM and CAE design have recently been introduced. These new methodologies represent the only significant advance in the dental arts for centuries. Pursuant to the new techniques, a dental prosthesis such as a bridge is machined or milled from a solid chunk of material under computer control. The milling is of both internal and external surfaces of adjacent dental substructures and proceeds generally from tooth position to tooth position. Upon reaching the final tooth position in a bridge array, numerous inaccuracies have arisen from the extensive milling or grinding.

OBJECTS OF THE INVENTION

An object of the present invention is to provide an improved method for producing dental prostheses.

Another object of the present invention is to provide such a method which is more ecomomical and efficient than conventional techniques.

Another, more particular, object of the present invention is to provide such a method which reduces the labor required.

Another particular object of the present invention is to provide such a method which reduces or substantially eliminates waste of precious metals.

A further particular object of the present invention is to provide such a method wherein several dental prostheses may be produced substantially simultaneously.

Yet another object of the present invention is to provide such a method which reduces the costs of producing prosthetic dental appliances.

An additional particular object of the present invention is to provide such a method which produces improved dental prosthesis and, more particularly, dental prostheses which are stronger, of a closer and more accurate fit, more durable and less prone to failure than conventional prosthetic dental devices.

Yet another object of the present invention is to provide a system for essentially automatically preparing prosthetic dental implants, restorations, splints, fixed bridges, crowns or inlays/overlays.

A further object of the present invention is to provide a mold assembly useful in producing prosthetic dental appliances.

SUMMARY OF THE INVENTION

A method for use in preparing a dental prosthesis comprises, in accordance with the present invention, the step of receiving an electrical signal encoding geometric specifications of a substructure of the prosthesis, the specifications including dimensions and shape of a tooth preparation at a dental site at which the prosthesis is to be affixed and the configuration of the substructure. In a subsequent step performed in response to the electrical signal, a computer is operated to automatically select a first mold component having a surface corresponding in dimensions to the tooth preparation and to automatically select a second mold component to produce, in cooperation with the first mold component, a mold cavity having dimensions and configuration corresponding to dimensions and configuration of the substructure. The first mold component and the second mold component are placed in predetermined relative positions to form the mold cavity and the mold cavity is filled with a quantity of a fluidic solidifiable dental material, i.e., a precious metal, a semiprecious alloy, a plastic composite, a porcelain glass material or any other usable dental restorative material.

Pursuant to another feature of the present invention, a metal form is removed from the mold cavity upon solidification of the fluidic solidifiable dental material with which the mold cavity is filled. The fluidic solidifiable dental material may take the form of liquid metal or a semi-solid metallic composition.

The filling step preferably comprises the step of introducing the fluidic solidifiable dental material into one of the mold components prior to the step of placing the mold components into juxtaposition with one another. In that event, the step of placing comprises the step of at least partially inserting the one mold component into the other mold component.

When the fluidic solidifiable dental material comprises a semisolid deformable mass, the step of placing comprises the steps of positioning the mold components on opposite sides of deformable mass and subsequently moving the mold components towards one another. The fluidic solidifiable dental material is thereby introduced into the mold cavity is sheared off of the deformable mass by the mold components during the movement of the mold components towards one another.

In accordance with an alternative embodiment of the present invention, the step of filling is performed subsequently to the placement of the first mold component and the second mold component in juxtaposition to one another to form the mold cavity. In that case, the step of filling comprises the step of injecting the fluidic solidifiable dental material (generally in a liquid form) into the mold cavity. In another alternative embodiment of the present invention, the mold cavity is filled while it is being formed. More specifically, the fluidic solidifiable dental material is poured or otherwise introduced into a mold form which is provided with the first mold component or the second mold component, the other of which is then closed over the molten metal or alloy during a mold closing step.

Pursuant to another feature of the present invention, the first mold component and/or the second mold component (an outer mold part partially surrounding the first mold component) is machined prior to the juxtaposition of those two mold components to form the mold cavity. The machining is preferably automatically implemented in response to the received electrical signal encoding specifications of the desired prosthetic dental device. The machining may be accomplished by any suitable technique, including electro-erosion, laser cutting, ultrasonic material removal, milling, grinding and/or drilling.

Preferably, too, the steps of juxtaposing the first mold component and the second mold component are performed automatically. More particularly, the computer is operated to control a robotic device to (a) place the first mold component and the second mold component in predetermined relative positions to form the mold cavity and (b) introduce into the mold cavity a quantity of a fluidic solidifiable dental material.

The placement step is accomplished by attaching the first mold component and the second mold component to respective mold supports and then positioning the mold supports relative to one another. One of the mold supports comprises a board provided with an array of predetermined positions for receiving the first mold component, while the other mold support comprises a board provided with an array of predetermined positions for receiving the second mold component.

The first mold component and the second mold component are each provided with a pin insertable into apertures in the respective mold support. More specifically, the first mold component and the second mold component are provided with a plurality of mounting pins, apertures for receiving the mounting pins being machined in a pair of mold support members.

Pursuant to another feature of the present invention, the electrical signal is transmitted via a telecommunications linkage. Alternatively, the the electrical signal is communicated via a transported memory element such as a floppy disk.

Pursuant to yet another feature of the present invention, either the first or the second mold component includes a mold body and an insert. The insert is possibly machined prior to the step of placing the mold components into juxtaposition with one another. The step of machining is preferably performed automatically in response to the electrical signal.

In accordance with a further feature of the present invention, the tooth preparation takes a post-like form and the first mold component includes a body with a base and a ring-shaped portion at the base. The ring-shaped portion is in one embodiment a separate piece attached to the body portion of the first mold component. The ring-shaped portion may be machined along an inner surface thereof to form with the body of the first mold component a skirt region of the mold cavity.

It is to be noted that the ring structure around the body portion of the first mold component may be an integral or unitary part of the body portion. Thus, each body shape of the first mold component may be duplicated several times over, each duplicate having a respective ring with a predetermined thickness, width, height and internal dimensions to define a respective skirt region of a mold cavity. In this way, only one mold need be cut after the closest fit is selected.

A prosthesis with a substructure manufactured in accordance with the present invention may take the form of an overlay such as a crown, a bridge or a splint.

According to another embodiment of the invention, a plurality of third mold components are disposed in a predetermined array determined in accordance with information contained in the electrical signal. In addition, a plurality of fourth mold components are positioned in a corresponding array also determined in accordance with information contained in the electrical signal. In this case, the afore-mentioned first mold component constitutes one of the third mold components and the second mold component constitutes one of the fourth mold components. More particularly, the third mold components are placed in the predetermined array on a first mold support and the fourth mold components are placed in the corresponding array on a second mold support.

A system for use in preparing a dental prosthesis comprises, in accordance with the present invention, a receiver component, a robot mechanism, a liquid introduction mechanism and a computer. The electrical signal arrives at the receiver component, for example, from a remote computer over telecommunications transmission lines or wireless transmission systems or from a floppy disk. The electrical signal encodes specifications of a substructure (e.g., metal portion) of the prosthesis, the specifications including dimensions of a tooth preparation at a dental site at which the prosthesis is to be affixed and configuration of the substructure.

The robot mechanism selects, in accordance with the electrical signal, a second mold component and a first mold component corresponding in dimensions to the tooth preparation and places the first mold component and the second mold component in predetermined relative positions to form a mold cavity. The filling mechanism introduces into the mold cavity a quantity of a fluidic solidifiable dental material. And the computer is operatively connected to the receiver component, the robot mechanism and the filling device for controlling and sequencing the operation thereof in response to the electrical signal.

A system in accordance with the present invention further may further comprise an extraction apparatus for removing a metal form from the mold cavity upon solidification of the fluidic solidifiable dental material with which the mold cavity is filled. The computer is operatively connected to the extraction apparatus for controlling the operation thereof.

Pursuant to another feature of the present invention, the system further comprises a cutting or grinding mechanism operatively connected to the computer for cutting or shaping, in response to signals therefrom, the first mold component and/or the second mold component prior to placement of the first mold component into juxtaposition to the second mold component.

A mold assembly for use in preparing a dental prosthesis comprises, in accordance with the present invention, a first mold component and a second mold component surrounding at least a part of the first mold component, at least one of the first mold component and the second mold component having a surface corresponding to a tooth preparation. The assembly further comprises a first mold support, first attachment elements for removably connecting the first mold component to the first mold support, a second mold support, and second attachment elements for removably connecting the second mold component to the second mold support. The assembly also comprises means for movably juxtaposing the first mold support to the second mold support so that the first mold component is located at least partially inside the second mold component.

Pursuant to another feature of the present invention, the first attachment elements and second attachment elements each include a pin element on one of the first mold component and the first mold support and an aperture on the other of the first mold component and the first mold support.

Pursuant to a further feature of the present invention, each of the mold supports comprises a board provided with an array of predetermined positions for receiving the respective one of the mold components.

According to additional features of the invention, the second mold component comprises a mold body defining a cavity and an insert piece inside the mold body, while the first mold component includes a mold body and a ring-shaped element secured to the mold body at a base thereof.

Another mold assembly for use in preparing a dental prosthesis comprising, in accordance with the present invention, a male mold component provided at a base side with an annular flange in turn provided with a ring shaped groove on a transversely extending face of the flange, the male mold component having a body portion with a surface corresponding to a tooth preparation, and a female mold component engageable with the flange to form a closed mold cavity in the form of a dental onlay. Preferably, the flange is removably attached to the male mold component. In addition, a removable insert is provided inside the female mold component.

Another mold assembly in accordance with the present invention comprises a plurality of male mold components and a plurality of female mold components each including a portion for surrounding at least a part of at least one of the male mold components. The male mold components are attached to a first mold support, while the female mold components are attached to a second mold support. At least one mold insert is positioned inside one of the female mold members. In addition, the mold assembly includes means for removably juxtaposing the first mold support to the second mold support so that the male mold components are located at least partially inside respective ones of the female mold components, each mating pair of the male mold components and the female mold components including at least one surface coresponding to a tooth preparation.

Pursuant to another feature of the present invention, the mating pairs of the male mold components and the female mold components form mold cavity portions corresponding to different teeth in the mouth of a single individual. The male mold components are juxtaposed to one another on the first mold support and the female mold components are juxtaposed to one another on the second mold support, whereby the male mold components and the female mold components cooperate to form a bridge.

Another, related method for manufacturing a customized dental prosthesis comprises, in accordance with the present invention, the steps of generating electrically encoded data representing a three-dimensional surface of a tooth to be restored, automatically feeding the data to a first computer, and operating the computer to generate an electrical signal encoding specifications of a substructure of the prosthesis. The specifications include dimensions of a tooth preparation at a dental site at which the prosthesis is to be affixed and configuration of the substructure. The electrical signal is transmitted to a second computer.

In a preferred embodiment of the present invention, the electrically encoded tooth surface data is generated by optically scanning the three-dimensional surface. Reference marks are provided on the three-dimensional surface as a step in the optical scanning process.

Alternatively or additionally, the three-dimensional surface data may be generated by (a) tracing a contour of the three-dimensional surfaces with a stylus-type instrument provided with an extension disposed outside of the mouth in which the tooth is located and (b) optically monitoring movements of a predetermined point on the extension.

If, on the one hand, the patient's tooth or teeth is prepared to form a tooth preparation prior to the gathering of the three-dimensional surface data, the specifications encoded in the transmitted electrical signal include actual dimensions of the tooth preparation. In this case, the computer receiving the electrical specification-encoding signal may be used to control machining operations on a selected first mold component (corresponding to the actual tooth preparation), as well as on the inner surface of a second mold component into which the machined first mold component is to be placed to form the mold cavity.

If, on the other hand, the tooth is not prepared prior to the generation and transmission of the specification-encoding signal, the specifications entail projections of the dimensions of the actual tooth preparation and the desired prosthetic appliance. These projected dimensions or specifications are derived by the first computer in accordance with instructions from the dental practitioner. These instructions may be entered into the first computer by any or all of several techniques, including the use of a keyboard, a mouse, a pantograph type indicator or video inputs.

Pursuant to another feature of the present invention, the first computer is operated to calculate a varying thickness dimension of the substructure of the prosthetic applicance so that a porcelain portion of the applicance or overlay has a substantially constant thickness throughout.

A method for producing dental prostheses in accordance with the present invention is more ecomomical and efficient than conventional techniques, in part owing to a reduction in labor costs and in part owing to an efficient, waste-minimizing use of precious metals.

In a method in accordance with the present invention, the substructures of several dental prostheses may be produced substantially simultaneously. The first mold components and second mold components corresponding to each prosthetic device are attached in a single mold assembly, the metal flow essentially filling all of the several mold cavities simultaneously. This technique further reduces costs by maximizing production runs.

Dental prostheses produced in accordance with the present invention are stronger, more accurately shaped, more durable and less prone to failure than conventional prosthetic dental devices inasmuch as the substructure of an entire bridge or splint may be produced as a single casting, without soldered joints, using pure metal, unmixed with foreign gases, particles or matter from prior castings.

Prostheses produced in accordance with the present invention are produced with a minimum of milling. Not only is milling or machining of the final product reduced significantly, if not entirely eliminated at least in a large number of cases, but also the machining of the mold components is reduced. In producing any dental prosthesis, prefabricated mold components are used whose operative surfaces are known within a high degree of tolerance. If any milling of the mold components is required, it is required only in limited areas or spots. The consequent reduction in machining throughout the entire process results in a stronger, more durable product with a better fit to the patient's jaw.

BRIEF DESCRIPTION OF THE DRAWING

FIG. 8 is an elevational view of a distal end of the embodiment of FIG. 7, taken in the direction of arrow VIII.

FIG. 9 is a plan view of a reference stylus usable in conjunction with the data generating device of FIGS. 3 and 7.

FIG. 10 is a plan view of another reference stylus usable in conjunction with the data generating device of FIGS. 3 and 7.

FIG. 11 is a partially diagrammatic perspective view of an embodiment of a contour data generating device shown in FIG. 1.

DETAILED DESCRIPTION

Figure 1:
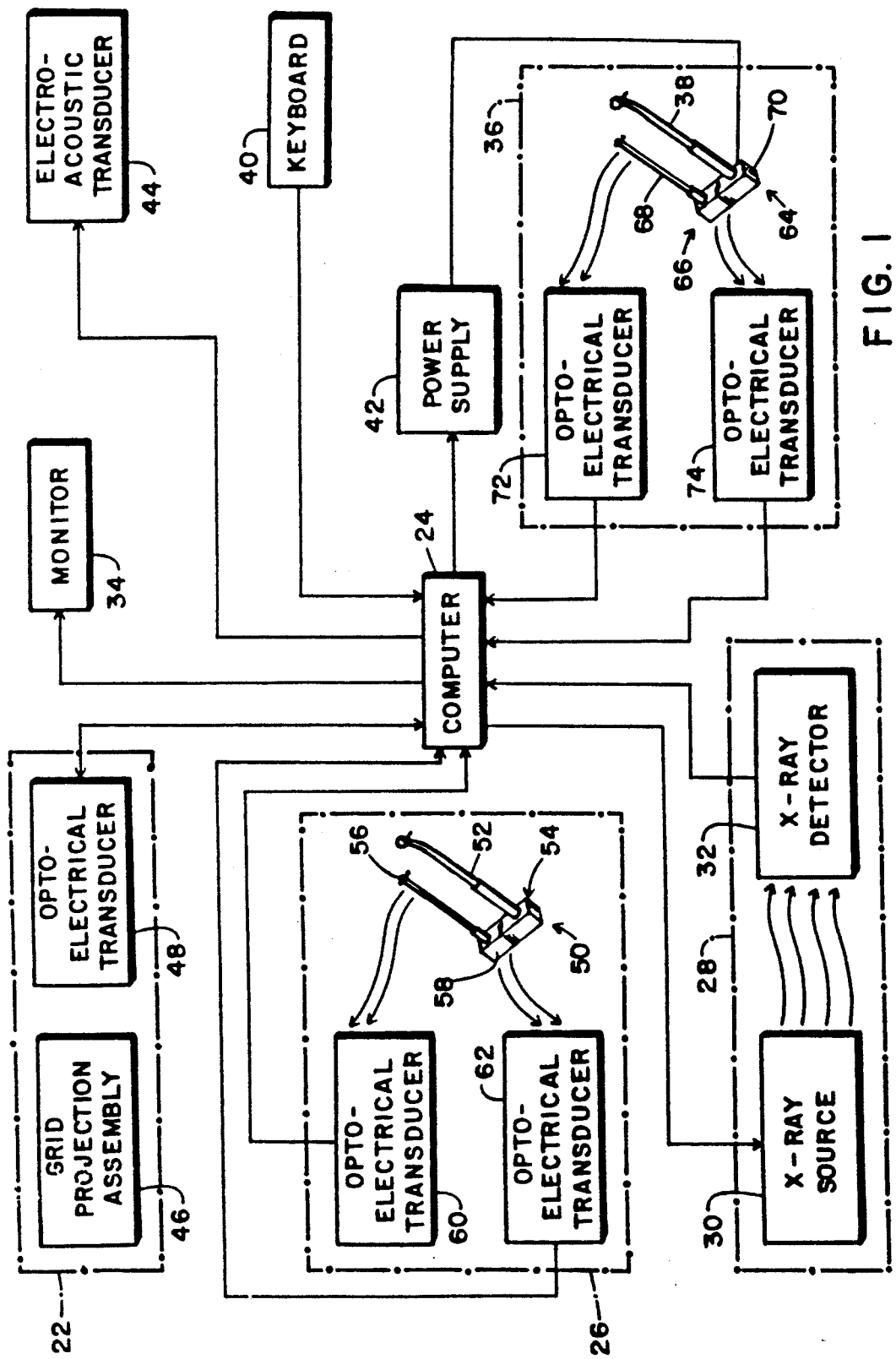
FIG. 1 is a block diagram of a system effecting a desired modification in the shape of a pre-existing object such as a tooth to which access is restricted.

As illustrated in FIG. 1, a computerized interactive system for producing a modification in the shape of an object such as a tooth to which access is limited comprises a first data generating device or assembly 22 for providing a computer 24 with electrically encoded data, specifically, digitized video signals representing a three-dimensional surface of an object such as a tooth. A second data generating device or assembly 26 is operatively connected to computer 24 for transmitting thereto digitized video signals containing information pertaining to a curvilinear contour on the surface of the three-dimensional surface of the tooth. In addition, computer 24 may receive from a third data generating device or assembly 28 digitized input signals relating to internal structures of the tooth being scanned. Specifically, data generating device 28 may take the form of an X-ray device such as used in current intra-oral radiology or other methodologies and basically comprises a source 30 of X-ray radiation and a detector 32 for receiving the X-ray radiation after it passes through a tooth and converting the incident radiation into a digital data stream fed to computer 24.

As further illustrated in FIG. 1, the computerized interactive dentistry system also comprises a display device 34 such as a monitor or holographic projector. In response to data signals, computer 24 generates a three-dimensional view on display of monitor 34 of the tooth or teeth under examination. More specifically, computer 24 is provided with any commercially available stereophotogrammetric triangulation program for calculating and displaying, on the basis of the video input signals from data generating devices 22, 26 and 28, three dimensional surfaces and contours of the tooth or teeth.

The computerized interactive dentistry system of FIG. 1 further includes another data generating device or assembly 36 which provides computer 24 with digitized video information as to the location of the operative tip of a cutting instrument 38 such as a dentist's drill relative to the three-dimensional structural features of the tooth. Data generating device 36 thus enables computer 24 to monitor modifications to the shape of the tooth as those modification are being made in the tooth.

The system of FIG. 1 is further provided with any of several instruction input devices such as a keyboard 40, a mouse (not shown), or a contact sensitive surface of monitor 34, whereby an operator such as a dentist or dental technician may instruct the computer to display a desired tooth preparation on monitor 34. In addition, or alternatively, computer 24 may use input from drill data generating device 36 as instructions regarding, for example, the depth of a tooth preparation to be displayed on monitor 34.

Upon selecting a desired tooth preparation illustrated on monitor 34, the dentist operates drill 38 to cut a recess into the tooth (in the case of a filling or inlay) or or to remove an outer layer of the tooth (in the case of preparing a form/shape for a crown or other prosthetic restoration). Computer 24 monitors the location of the operating tip of the drill via data generating device 36 and, if the drill approaches a boundary previously defined to the computer during an interactive tooth preparation selection operation, either interrupts the power provided to the drill via a supply 42 or alerts the dentist via a signaling device such as an electro-acoustic transducer 44.

As depicted schematically in FIG. 1 and discussed in greater detail hereinafter, data generating device 22 includes a grid projection assembly 46 for optically imposing a grid onto the surface of the patient's tooth. Data generating device 22 also includes an opto-electrical transducer 48 such as a charge-coupled device for optically sensing or scanning the tooth surface onto which the grid is projected by assembly 46. It is to be understood that the grid pattern projected on the tooth surface need not be an orthogonal grid having two sets of lines at right angles to one another, but may instead have the two sets of lines oriented at an acute angle. Moreover, although the preferred embodiments of the present invention incorporate an optical grid, it is to be appreciated that the invention also contemplates that a grid may be imposed onto the tooth surface by other methods, such as adhesively attaching to the tooth surface a transparency provided with a grid. In addition, the grid provided on such a transparency need not take the specific form of two sets of orthogonal lines but may instead take the form of an array of virtually any shapes, such as dots or circles. It is only necessary that the precise size of the shapes be known and programmed into the computer.

As further depicted in FIG. 1 and described in detail hereinafter, data generating device 26 comprises a pantograph-type component 50 which incorporates a stylus member 52 and a pantograph extension 54 in turn including a pantograph arm 56 and a bridge element 58. Bridge element 58 connects pantograph arm 56 to stylus member 52. Data generating device 26 further comprises at least a pair of opto-electrical transducers 60 and 62 preferably in the form of respective charge-coupled devices ("CCD"s). Pantograph component 50 enables computer 24 to track, from outside the mouth, the motions of the tip of the stylus member inside the mouth and even beneath the gum line.

Accordingly, data generating devices 22, 26 and 28 provide to computer 22 electrically encoded data completely defining the structure of the tooth on which a dentist is working. Computer 24 then "draws" the tooth on monitor 34. At that juncture the dentist instructs the computer to modify the displayed three-dimensional shape. For example, the dentist may use keyboard 40 to input a command that a predefined tooth preparation, in graphic form, be overlaid on the three-dimensional graphic representation of the tooth. The size of the tooth preparation relative to the tooth may be specified by entering a depth dimension via keyboard 40, data generating device 36, a mouse or a contact-sensitive surface of monitor 34. Alternatively, computer 24 may be programmed to automatically select a possible tooth preparation in accordance with the data from data generating devices 22, 26 and 28. In accordance with yet another alternative procedure, the dentist may command the computer to alter the graphic representation of the tooth, for example, by removing a layer of several millimeters from a surface selected by the dentist or by removing a selected volume of tooth from all five surfaces above the gum line to a contour below the gum line defined by the second data generating device 26.

As further depicted in FIG. 1 and described in detail hereinafter, data generating device 36 comprises a pantograph-type component 64 which incorporates drill 38 and a pantograph extension 66 in turn including a pantograph arm 68 and a bridge element 70. Bridge element 70 connects pantograph arm 68 to drill 38. Data generating device 36 further comprises at least a pair of opto-electrical transducers 72 and 74 preferably in the form of respective charge-coupled devices ("CCD"s). Pantograph component 64 enables computer 24 to track, from outside the mouth, the motions of the tip of drill 38 inside the mouth and even inside a tooth.

In a preferred form of the system described herein, data generating device 36 is the same as data generating device 26 with stylus element 52 replaced by drill 38. Moreover, upon the selection of a desired tooth preparation via computer 24, monitor 34 and an instruction input device such as keyboard 40, drill 38 is used by the dentist to provide the displayed tooth preparation in the subject tooth. Computer 24 monitors the output signals of opto-electrical transducers 72 and 74 thereby tracks the cutting motions of the operating tip of drill 38 inside the subject tooth. The excavations into the tooth are displayed in real time on monitor 34 by computer 24.

Figure 2:
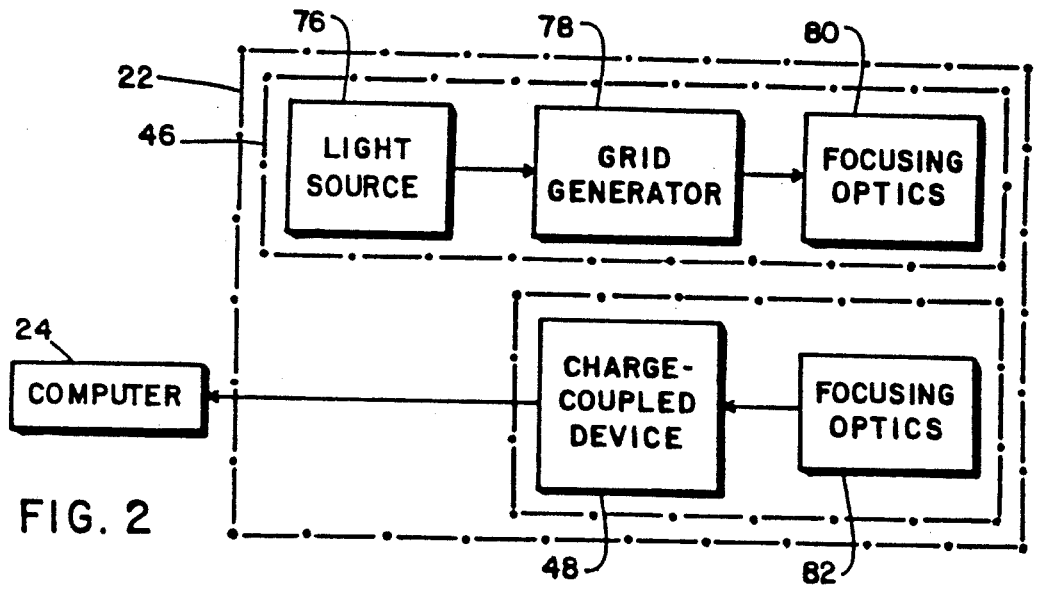
FIG. 2 is a block diagram showing details of a surface data generating device shown in FIG. 1.

As shown in FIG. 2, grid projection assembly 46 of data generating device 22 includes a light source 76, a grid generator 78 and an assembly 80 of light guides and lenses for guiding the grid light along a path through the data generating device and for focusing the grid light on the surface of a subject tooth. The light subsequently reflected from the tooth surface is gathered by further optical elements 82 and focused by those elements on the light sensitive sensor surface of charge-coupled device ("CCD") 48. In response to a sensed pattern of light intensities, CCD 48 generates and transmits to computer 24 a digitized video signal containing information used by computer 24 to calculate the dimensions of the subject tooth and to display the tooth's structure in a three-dimensional graphic representation on monitor 34.

Figure 3:
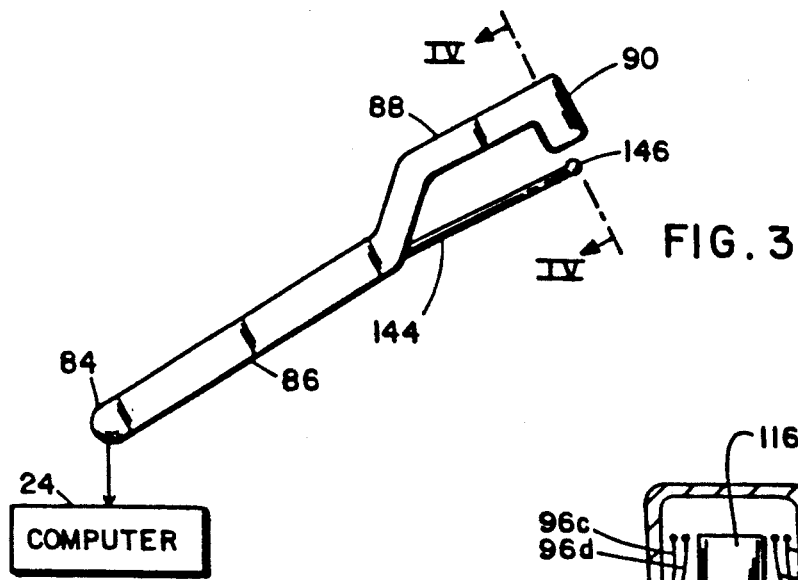
FIG. 3 is partially a block diagram and partially a schematic elevational view of a particular embodiment of the surface data generating device of FIG. 2.

As shown in FIG. 3, the components 76, 78, 80, 82 and 48 of data generating device 22 may be housed in an elongate instrument frame or holder 84 including a handle 86 and a stem portion 88 displaced laterally with respect to a longitudinal axis of handle 86.

Figure 4:
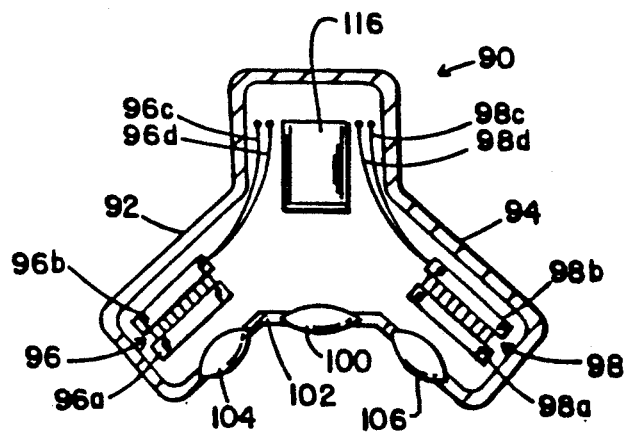
FIG. 4 is a cross-sectional view taken along line IV—IV in FIG. 3.

In a preferred form of the grid projection instrument, illustrated in detail in FIG. 4, holder 84 of FIG. 3 further includes a Y-shaped distal end portion 90 having a pair of hollow legs 92 and 94 housing respective CCDs 96 and 98. Each CCD includes a respective photosensitive sensor array 96a and 98b and respective sequencing and processing electronics 96b and 98b. The sequencing and processing electronics 96b and 98b have input and output leads 96c, 96d and 98c, 98d extending to computer 24 through stem portion 88.

Light containing a grid pattern is projected from Y-shaped distal end portion 90 through a focusing lens 100 mounted in a wall 102 between legs 92 and 94. The light subsequently reflected from a subject tooth is focused on sensor arrays 96a and 98a by a pair of lenses 104 and 106 disposed in legs 92 and 94. Lenses 104 and 106 may be considered parts of focusing optics 82 (FIG. 2), while lens 100 is part of focusing optics assembly 80.

Figure 5:
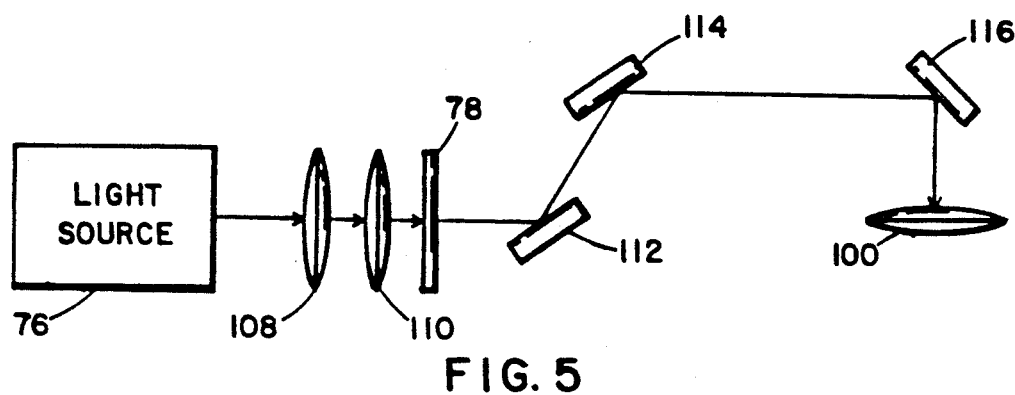
FIG. 5 is a detailed schematic diagram of optical components in a grid projection assembly included in the surface data generating device of FIG. 3.

As shown in detail in FIG. 5, grid projection assembly 46 includes light source 76 (also shown in FIG. 2), a pair of collimating lenses 108 and 110, grid generator 78 (see FIG. 2) in the form of a plate provided with a grid pattern, and three mirrors or prisms 112, 114, 116 for directing the grid-containing light rays through stem portion 88 (FIG. 3) to lens 100. Of course, frame or holder 84 may be provided with various movable mounting elements (not shown) for adjusting the focuses of the various lenses.

Figure 6:
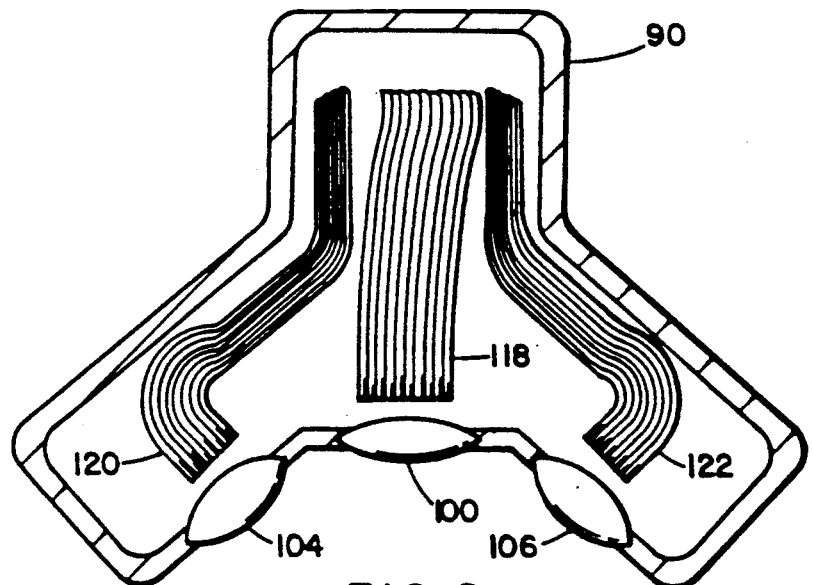
FIG. 6 is a cross-sectional view, similar to FIG. 4, of another particular embodiment of the surface data generating device of FIG. 2.

The grid light may be guided through the grid projection instrument or frame 84 by elements other than those illustrated in FIG. 5. As depicted in FIG. 6, an output array of light beams is guided to lens 100 by a bundle 118 of optical fibers, while a pair of optical fiber input bundles 120 and 122 receive incoming optical radiation focused on the input ends of bundles by lenses 104 and 108.

Fiber bundles 120 and 12 guide the incoming radiation to a pair of CCDs (not shown) disposed in instrument frame 90 at a more proximal end of the frame, for example, in the handle. Rather than two separate CCDs, the first data generating device 22 may include a single CCD (not shown) disposed in the handle 84 (FIG. 3) and means for directing light from two separate optical pathways to the CCD.

Figure 7:
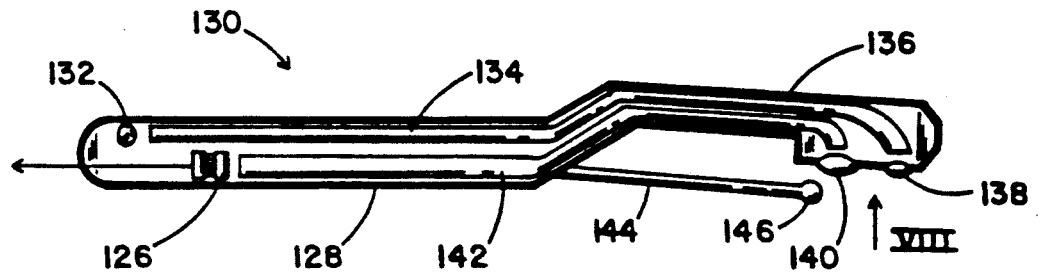
FIG. 7 is a schematic cross-sectional longitudinal view of yet another particular embodiment of the surface data generating device of FIG. 2.

As schematically shown in FIGS. 7 and 8, a data generating device or optical probe 124 may incorporate a single CCD transducer 126 disposed in a handle 128 of an elongate instrument frame or casing 130. The handle 128 also houses a grid source 132. An optical fiber bundle 134 guides a grid pattern from grid source 132 through a part of handle 128 and a stem portion 136 of frame 130 to a distal end of the probe. At the distal end, the grid pattern is focused by a lens 138 onto a subject tooth, the reflected radiation pattern being focused by another lens 140 onto the distal or input end of another fiber optic bundle 142 extending to CCD 126.

As shown in FIGS. 3 and 7, frame member 84 and optical probe frame 130 are provided with a stylus element 144 having an enlargement 146 at its distal end. Enlargement 146 is disposable in the visual field of the respective optical scanning element or elements, whether CCD 48, CCDs 96 and 98, or CCD 126, for providing computer 24 with a reference distance or dimension at the surface of a subject tooth being scanned. Computer 24 is thereby able to calculate absolute values for the dimensions of various surface features. Computer 24 measures distances by calculating the number of pixels in the respective sensor array (e.g., 96a and 98a) which cover a feature whose dimensions are being determined. Inasmuch as computer 24 is preloaded with the actual dimensions of enlargement 146, the computer is able to compute actual distances by comparing the number of pixels corresponding to enlargement 146 with the number of pixels corresponding to the features of the tooth.

Stylus element 144 is retractable into handle 86 or 128. Retraction may be implemented either manually or automatically, for example, by a small motor and rack and pinion (not illustrated) inside the respective handle. Moreover, stylus 144 is advantageously replaceable by other elements such as stylus 148 shown in FIG. 9 or stylus 150 shown in FIG. 10.

Stylus 148 is formed at a distal end with three prongs 152, 154 and 156 each having a respective sphere 158, 160 and 162 at its free end. Spheres 158, 160 and 162 may have different sizes for facilitating the measurement of anatomical distances by computer 24. Similarly, stylus 150 has a plurality of prongs 164, 166, 168, 170 and 172 each provided at its free end with an enlarged formation 174, 176, 178, 180 and 182 of a respective geometric shape and a respective transverse dimension.

In using a data generating device equipped with stylus 148, a dentist places at least two of spheres 158, 160 and 162 on the surface of the tooth. Similarly, two enlarged end formations 174, 176, 178, 180 and 182 are positioned in engagement with a tooth surface during use of a data generating device incorporating stylus 150.

Figures 12, 13, 14:
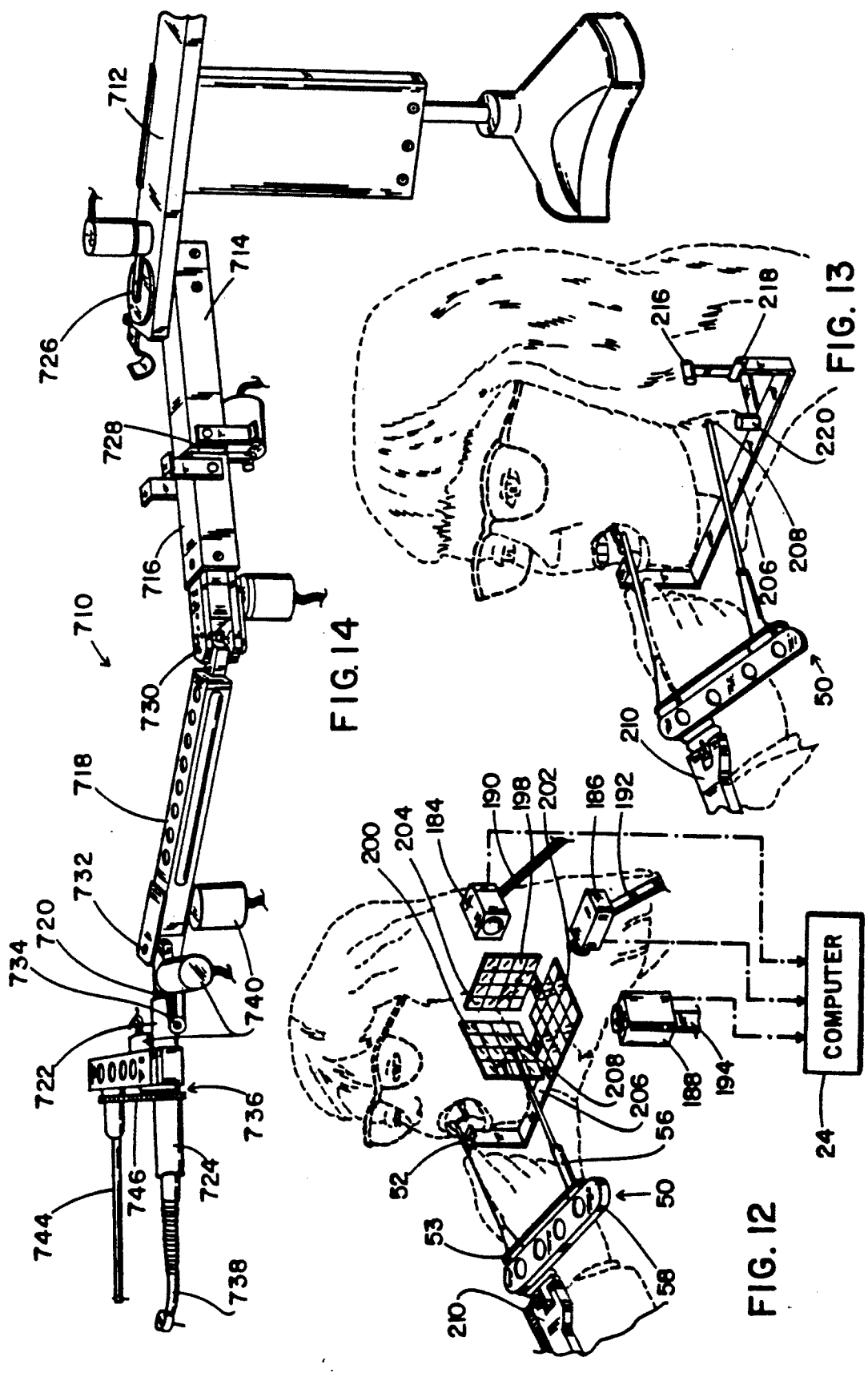
FIG. 12 is a partial perspective view, on an enlarged scale, of the contour generating device of FIG. 11, showing its use with a dental patient.
FIG. 13 is a partial perspective view, on an even larger scale, of another embodiment of the contour generating device of FIG. 1, showing its use with a dental patient.
FIG. 14 is a perspective view of another contour data generating device usable in a dentistry system.

As depicted in FIGS. 11 and 12, contour data generating device 26 (FIG. 1) comprises three CCD cameras 184, 186 and 188 fixed to the free ends of respective adjustable mounting arms 190, 192 and 194 in turn connected at their other ends to a pedestal member 196. Contour data generating device 26 further comprises three transparent plates 198, 200 and 202 each provided with a respective grid 204 (only one designated in the drawing) and secured to a common substantially L-shaped support arm 206. Support arm 206 is cemented or otherwise attached to the jaw of a patient P prior to the use of the contour data generating device.

It is to be noted that although plates 198, 200 and 202 are illustrated as being orthogonally disposed and as having Cartesian orthogonal grids, it is not necessary for effective calculation of distances and angles that the plates and grids be so oriented. An ordinary modification of the stereophotogrammetric triangulation program is all that is required for the system of FIG. 1 to function with plates 198, 200 and 202 and/or the grid lines thereof oriented at acute angles.

Any two CCD cameras 184, 186 and 188 correspond to opto-electrical transducers 60 and 62 of FIG. 1. Although three CCD cameras are preferred, in some instances two may be sufficient.

As further illustrated in FIGS. 11 and 12, contour data generating device 26 includes pantograph-type component 50. As described hereinabove with reference to FIG. 1 (includes essentially a mirror image of illustrations in FIG. 11 and 12), pantograph component 50 incorporates stylus member 52, pantograph arm 56 and bridge element 58 CCD Cameras 184, 186 and 188 enable computer 24 to track orthogonal components of the motion of a predetermined point 208 on pantograph arm 56 against respective reference frame plates 198, 200 and 200, respectively. Because pantograph arm 56 is fixed with respect to stylus member 52, computer 24 is accordingly able to track, from outside the mouth of patient P, the motions of the tip of the stylus member 52 inside the mouth and even beneath the gum line.

Pantograph component 50 is mounted to the free end of a linkage 210 including a plurality of pivotably interconnected arm members 212. The base of linkage 210, like pedestal member 196 is secured to a base 214.

Both stylus member 52 and pantograph arm 56 are rotatably secured to bridge element 58 so that they can rotate about respective longitudinal axes. Pantograph arm 56 is coupled to stylus member 52 via an endless toothed belt 53 whereby rotation of stylus arm 52 about its longitudinal axis by an operator results in a simultaneous rotary motion of pantograph arm 56.

Accordingly, stylus member 52 is free to be moved by an operator along three translational axes and three rotational axes, the resulting motion being duplicated by pantograph arm 56.

An alternative way for providing computer 24 with a reference frame against which to measure motions of pantograph arm 56 and concomitantly stylus member 52 is illustrated in FIG. 13. In the specific embodiment shown in FIG. 13, three CCD cameras 216, 218 and 220 are fastened to support member 206 in turn cementable, as discussed above, to the patient's jaw in which the subject tooth is rooted. Pursuant to this embodiment of the contour data generating device, no reference grids are necessary for computer 24 to monitor, via cameras 216, 218 and 220, the motion of pantograph arm 56 and thus stylus member 52.

It is to be noted that the camera assembly of FIG. 13 essentially includes three pixel arrays (not visible in the drawing) disposed in separate reference planes of a three dimensional coordinate system, with the casings of the cameras serving in part to hold three lenses (not designated with reference numerals) at pre-established distances with respect to the respective pixel arrays to focus the light from the tip 208 of the pantograph arm on the pixel arrays. The tip 208 of pantograph arm 56 may be provided with an LED or other marker element to facilitate detection by the optical scanning assembly comprising cameras 216, 218 and 220.

As illustrated in FIG. 14, contour data may be generated by an alternative technique employing a multiple segment support arm 710 which extends from a fixed platform 712. Support arm 710 includes segments 714, 716, 718, 720, 722, and 724 of which the first segment 714 is connected to platform 712. Segments 714–724 are pivotably connected to one another via six rotating joints, 726, 728, 730, 732, 734 and 736. By incorporating six separate junctions for rotational movement, an operating instrument (e.g., drill) 738 connected to the free end of a last or outermost arm 724 can move with six degrees of freedom, specifically along three translational axes and three rotational axes.

Stationary platform 712 and segment 714 are connected at joint 726 to provide rotation relative to one another about a substantially vertical axis. First segment 714 and second segment 716 are coupled to one another for rotation about an axis which is essentially a horizontal axis and which axis is co-extensive with the axes of segments 714 and 716. Joint 728 provides this rotational movement. Similarly, arm segments 716 and 718 are rotatably linked via joint 730.

A probe or pantograph-type extension 744 is mounted to the outermost segment 724 and through a belt 746 rotates in synchronism with operating instrument 738. In this fashion, probe 744 is slaved to operating instrument 738. Accordingly, a three-dimensional configuration or contour traced by the tip of operating instrument 738 will be replicated by a tip of pantograph extension 744.

Each joint 726-736 is formed to have sufficient friction to allow the joint to hold a position once placed therein. However, the friction of each joint is low enough so that movement of the joint can be commenced fairly easily.

A plurality of digital encoders 740 are mounted to arm segments 714-724. Upon a movement of operating instrument 738, encoders 740 transmit to computer 24 respective signals encoding the amount of motion in the various six degrees of freedom. The monitoring device of FIG. 14 need not include pantograph extension 744 since motion tracking is accomplished via the encoder output signals rather than optically.

Upon the transmission to computer 24 of sufficient data from surface data generating device 22 and contour data generating device 26 (FIG. 1), computer displays partial or complete graphic representations on monitor 34 of the subject tooth or teeth. The graphic representations include the visible three-dimensional surfaces of each such tooth, as well as invisible base line data fed to computer 24 by contour data generating device 26. In addition, computer 24 may be provided with electrically encoded data specifying internal structures such as the dentine inside each tooth and prior fillings or other prosthetic devices.

Upon viewing a tooth on monitor 34, a dentist may select a preparation which may be appropriate for the particular condition of the tooth. As described above, this selection may be accomplished via an instruction corresponding to an electrically encoded tooth preparation previously loaded into the memory of computer 24. Alternatively, the selection may be implemented by inputting dimensional parameters via keyboard 40, including distances, angles, planes and percentages. As another alternative, computer 24 may provide a menu selection on monitor 34, selections being made from the menu via the keyboard, a mouse or a touch-sensitive monitor screen. In yet another alternative procedure, computer 24 may be programmed to recognize structural features of the tooth, such as its type, the location and shapes of cavities and prior inlays or onlays and to automatically select a possible preparation in accordance with the recognized features. The computer may be further programmed to vary the size of the preparation to correspond to the particular tooth. The dentist would then view the selected preparation and alter it on screen by any of the above-described instruction input techniques. Upon arriving at a final, desired preparation, the dentist will inform computer via keyboard 40.

As discussed hereinabove, drill 38 (FIG. 1) is then used to remove a portion of the subject tooth. Computer 24 may control the supply of power to the drill so that the drill is operational only within the regions selected for removal during the interactive stage of the dental process. Accordingly, drill 38 will be de-energized until the cutting tip of the drill is in near engagement with a surface to be cut. Then computer 24 enables the transmission of power from supply 42 to drill 38. Upon the subsequent approach of the cutting tip of the drill to a defined boundary, as sensed preferably via data generating device 46 (FIG. 1), i.e., via CCD cameras 184, 186, 188 or 216, 218, 220 monitoring a pantograph component 50, computer 24 automatically interrupts power transmission from supply 42 to drill 38.

Figure 15:
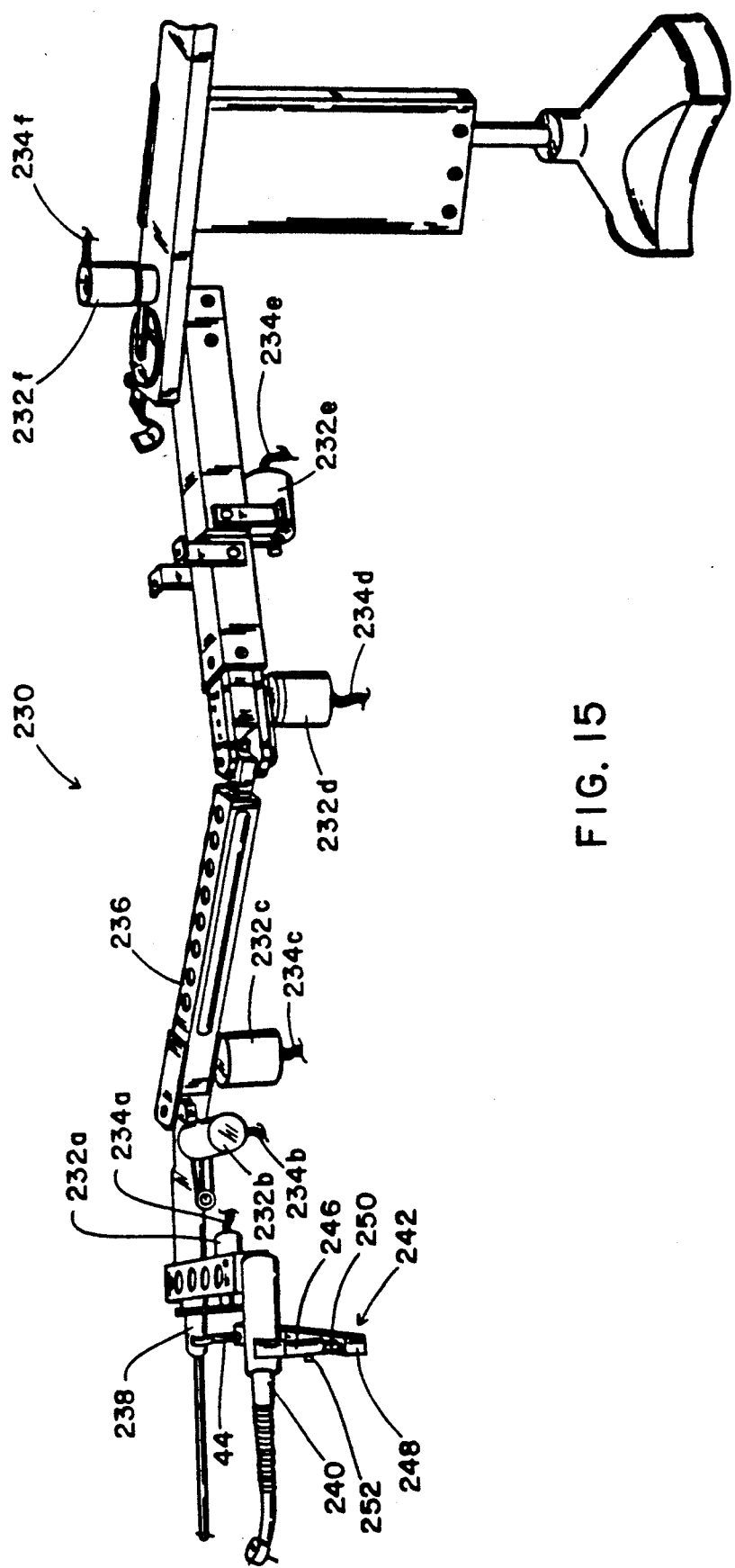
FIG. 15 is a perspective view of drill movement control assembly.

FIG. 15 illustrates a drill movement control assembly 230 similar in geometric design to the linkage 226 of FIG. 14. However, the encoders 22 of that linkage mechanism have been replaced in the movement control assembly of FIG. 15 with motors $232a$-$232f$ connected via respective energization leads $234a$-$234f$ to computer 24 (FIG. 1). In addition, in drill movement control assembly 230, the free end of a linkage 236 is connected to a pantograph arm 238 rather than to a drill member 240. Drill member 240 is rigidly but removably coupled to pantograph arm 238 via a U-shaped bridge 242 including a pair of legs 244 and 246 fastened to pantograph arm 238 and drill 240, respectively, and a transverse connector piece 248. Yet another leg member 250 is rigid with connector piece 248 and is telescopingly received inside leg 246. A spring loaded release latch 252 serves to removably clamp leg member 250 inside leg 246. Release latch 252 constitutes a safety mechanism enabling a dentist to remove drill 240 from a patient's mouth if the motion of the drill therein in response to operation of motors $232a$-$232f$ by computer 24 is not satisfactory to the dentist.

Upon the selection of a desired or optimum tooth preparation by a dentist and a subsequent signal for commencing tooth cutting, computer 24 generates a series of signals selectively energizing motors $232a$-$232f$ to move the operative end of drill 240 into engagement with those regions of the subject tooth which are to be removed to achieve the desired preparation. As described hereinabove, computer 24 controls the energization of drill 240 so that the drill is operative only in preselected zones in and about the regions of tooth to be removed.

Figure 16:
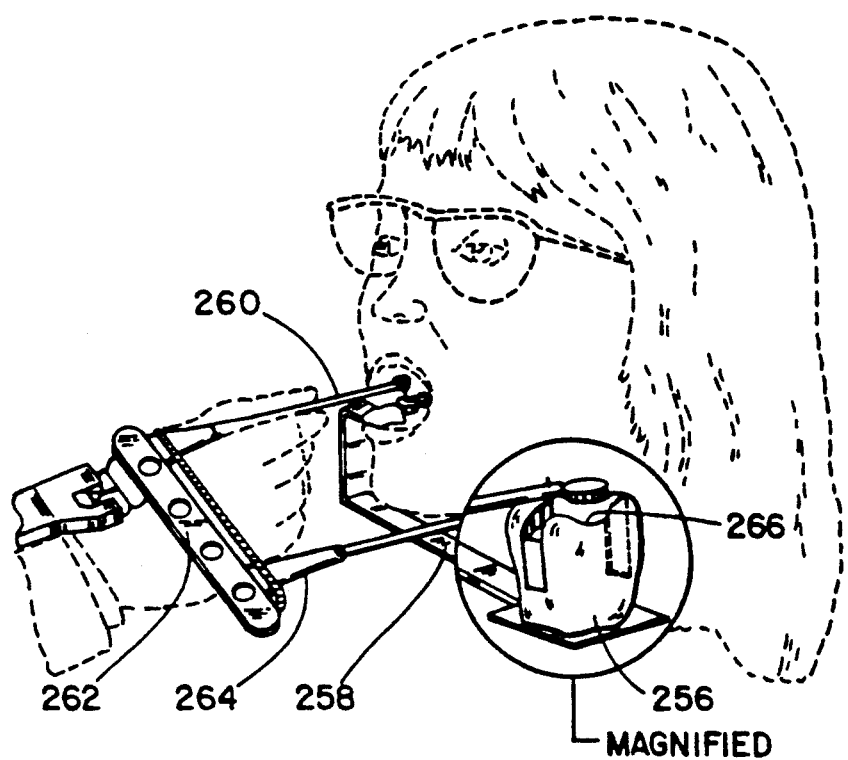
FIG. 16 is a partial perspective view, on an enlarged scale, of a drill movement restriction assembly, showing a tooth preparation preform on an even larger scale.

Limiting the motion of a dentist's drill 254 may be accomplished by selecting a tooth preparation preform 256 from a kit of preforms (see FIG. 16). Preform 256 may be selected by computer 24, as described above, to conform to a desired preparation or may be manually selected. Preform 256 is cemented to one end of a support bracket 258, the other end of which is attached to the patient's jaw wherein is rooted a tooth to be provided with the preparation of the selected preform. A pantograph assembly including a drill 260, a bridge member 262 and a pantograph arm 264 is then used to cut the tooth. A tip on the pantograph arm corresponding to the cutting tip of drill 260 is inserted into a cavity 266 in preform 256 (in the case of a filling or inlay). Engagement of the tip of pantograph arm 264 with the walls of cavity or recess 266 limits the concomitant motion of the drill, whereby the tooth is provided with a recess having the same geometric structure as recess 266.

Accordingly, a kit is provided of dental preparation preforms in different sizes and shapes. Some preforms correspond to inlays such as that shown in FIG. 16. Other preforms correspond to onlays or crowns. The kit may also include prefabricated prosthetic devices, that is, preformed inlays and onlays for attachment to tooth surfaces upon preparation of those surfaces as described hereinabove.

Computer 24 has a data memory loaded with electrically encoded data corresponding to all of the preformed inlays and onlays in the kit. More specifically, the predefined tooth preparations selectable automatically by computer 24 or in response to instructions received via keyboard 40 or otherwise all correspond to respective prosthetic inserts of several predefined sizes.

Accordingly, computer 24 operates to select a desired tooth preparation and to control the formation of that preparation in the subject tooth. Upon the completion of the preparation, either the computer or the dentist selects the appropriately sized inlay or onlay. If necessary in a particular case, a selected preformed inlay or onlay can be machined prior to attachment to a tooth. Computer 24 may control the machining operations in a conventional numerically controlled operation or may serve to limit the range of cutting motions, as described hereinabove with reference to providing a tooth with the desired preparation.

Figure 17:
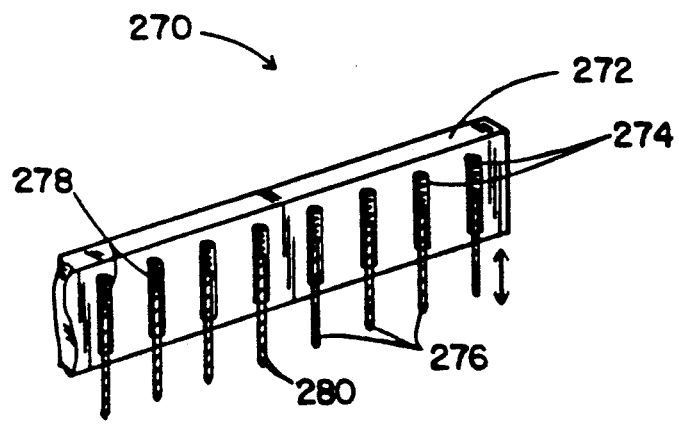
FIG. 17 is a partial schematic perspective view of a reference marker assembly.

FIG. 17 shows an assembly 270 for supplying surface data generating device 22 (FIG. 1) with optically detectable reference distances or displacements at the surface of the object (such as a tooth). Assembly 270 is attachable to the distal end of a dental probe such as instrument frame or holder 84 and comprises a holder member 272 made of transparent material and provided with a linear array of equispaced parallel bores 274 each slidably receiving a respective reference pin or stylus 276. Each stylus is pushed outwardly in a transverse direction relative to holder member 272 by a respective compression spring 278. In addition, each stylus 276 is provided with a series of longitudinally equispaced striations or reference marks 280.

The extensions of styli 276, i.e., the lengths to which the styli are pushed inside holder member 272, are measured by computer 24 through video signals obtained via a pair of optical pathways such as those illustrated in FIGS. 4 and 6. Alternatively, two optical light receiving elements such as prisms (not shown) may be placed on the same lateral side of the stylus array.

In using reference generator assembly 270 of FIG. 17, an operator such as a dentist presses styli 276 against a tooth surface. Under the pressure exerted by the operator, styli 276 are pushed respective distances into bores 274 against the action of springs 278. The displacement of each stylus 276 depends on and is a measure of a height of a respective surface element or zone of the tooth surface.

In most instances only a few (possibly as few as two) different positionings of stylus assembly 270 are required for computer 24 to map the entire surface of the tooth under observation.

Figure 18:
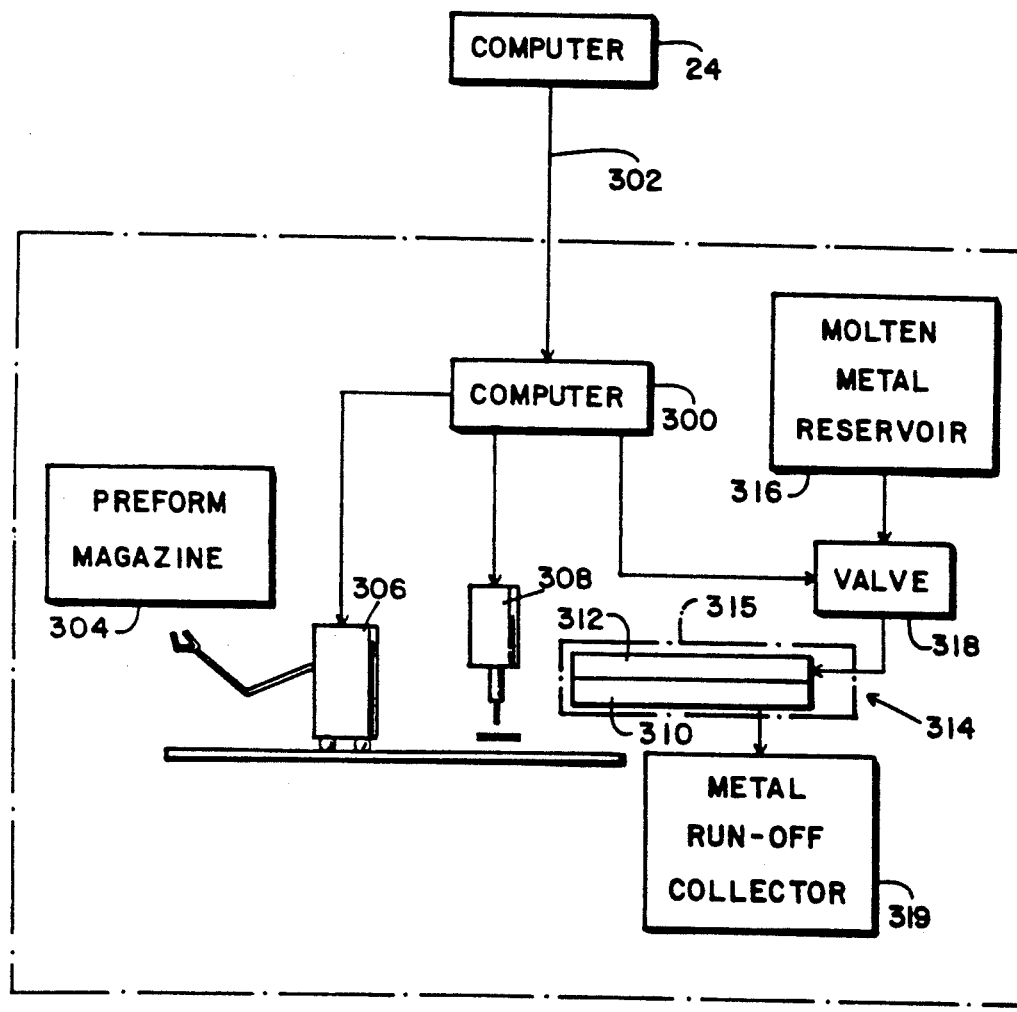
FIG. 18 is a diagram of a system for manufacturing a dental prosthesis, in accordance with the present invention, particularly for manufacturing a metal or alloy substructure of the prosthesis.

As illustrated in FIG. 18, to manufacture a metallic substructure of a dental prosthesis such as a crown, bridge or filling, computer 24 is operatively connected to another computer 300 at a remote location via a telecommunications link 302 such as the telephone lines. In response to an instruction from an operator, computer 24 transmits to computer 300 an electrical signal encoding geometric specifications of the metallic substructure of the prosthesis. The specifications include the dimensions and shape of a tooth preparation at a dental site at which the prosthesis is to be affixed and configuration of the substructure. More particularly, in the event that the dental practitioner wishes to provide a tooth with a crown, the three-dimensional surface of a preparation of the tooth is encoded by computer 24 and transmitted as part of an order signal to the remote computer 300.

As described hereinabove, the three-dimensional surface data of the tooth preparation may be derived from three-dimensional data of the tooth by instructing the computer to modify the tooth surface data to produce, in electronic form and as visually presented on monitor 34 (FIG. 1), a desired tooth preparation. The computer may be instructed, for example, via keyboard 40 (FIG. 1), a mouse (not shown), or a contact sensitive surface of monitor 34, to remove from the electronic representation of the tooth a respective percentage of the dental matter from each surface of the tooth. Other methods of generating electrical data representing a three-dimensional surface of a desired tooth preparation are discussed in detail hereinabove. Alternatively, the tooth may actually be prepared, the electrical signal transmitted to remote computer 300 from computer 24 in that case corresponding to an actual preparation, rather than a planned preparation. The three-dimensional surface data of the actual tooth preparation may be accumulated by any of the methods described above.

The electrical data transmitted from computer 24 to computer 300 also includes a specification of the type and thickness of the crown or other dental prosthesis for which the dental practitioner is placing an order.

Computer 300 is located at a manufacturing facility which maintains in a store or magazine 304 an inventory of dental mold preforms corresponding to a multiplicity of tooth preparations for each tooth position. The preform magazine also includes a multiplicity of cooperating preforms each serving to define the outer surface (opposite the prepared tooth surface) of a metallic portion of a respective dental prosthesis substructure. Computer 300 maintains a registry of all the available preforms.

Figure 19:
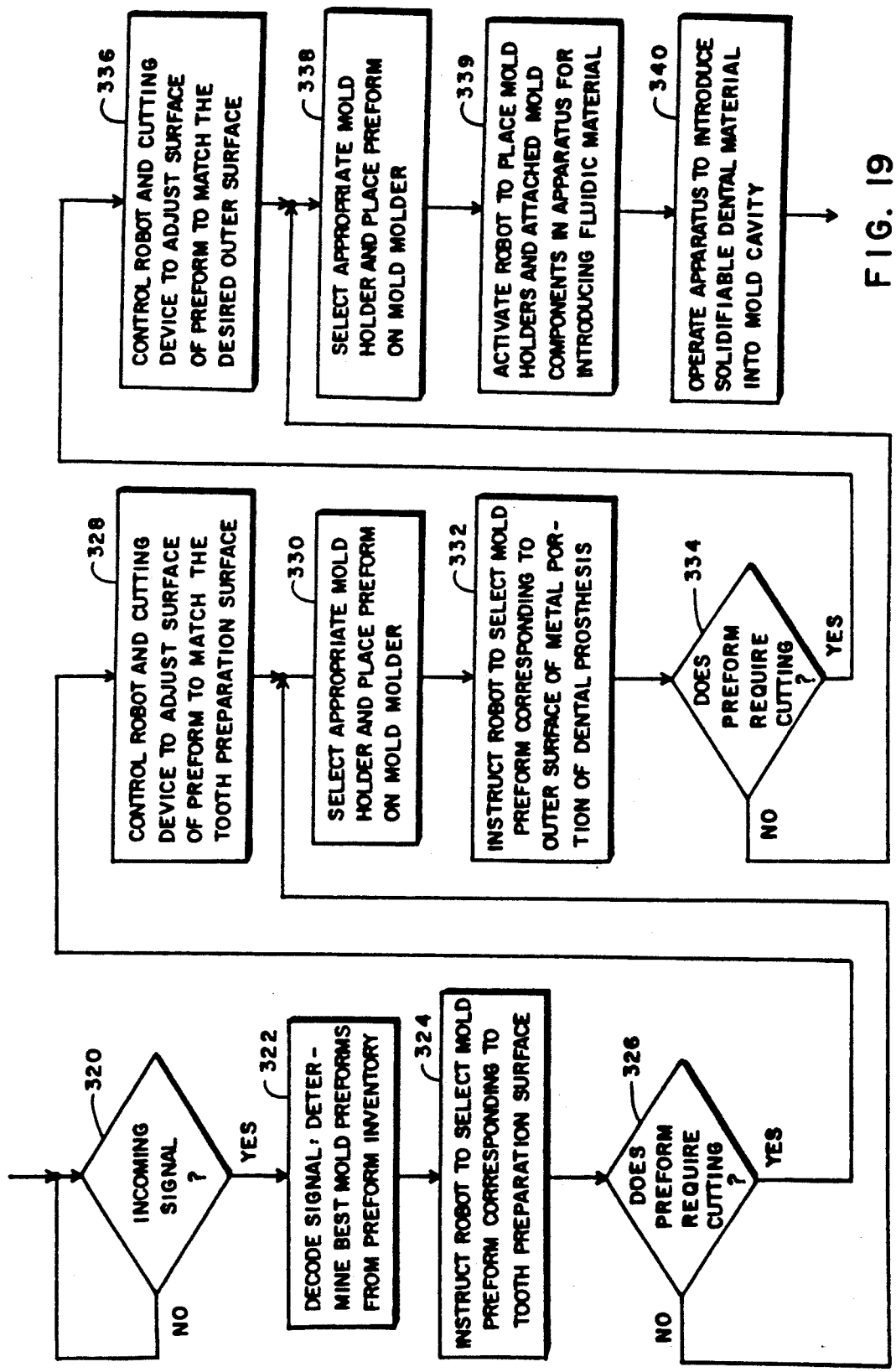
FIG. 19 is a flow chart showing successive steps in the operation of a control unit or computer in the system of FIG. 18.

As indicated in FIG. 19, computer 300 monitors telecommunications link 302 in a recurring step 320 to determine whether an order has arrived for a dental prosthesis. Upon detecting such an order, computer 300 decodes the signal in a step 322 and in response to the information contained in the signal, selects a mold preform from magazine or store 304 which corresponds most closely to the three-dimensional dental preparation encoded in the received signal. Upon making the selection from its memory banks, computer 300 instructs a robot mechanism 306 (FIG. 18) in a step 324 (FIG. 19) to physically obtain the selected mold preform from magazine 304.

In an inquiry 326, computer 300 determines whether the selected mold preform has a three-dimensional molding surface corresponding identically to the three-dimensional tooth preparation or whether the mold preform requires machining to attain the exact surface required. If machining is necessary, computer 300 instructs (in a step 328) robot mechanism 306 to place the preform in a cutting device 308. Computer 300 then operates the cutting device to machine the preform mold until the correct surface characteristics are attained.

In a subsequent step 330, computer 300 generates an output signal controlling robot mechanism 306 to select a mold holder or support 310 for the preform and to place the machined preform thereon.

Computer 300 then scans its memory banks for a cooperating preform in magazine 304 having a surface most closely corresponding to the outer surface (opposite the tooth preparation surface) and configuration of the desired dental prosthesis substructure, as encoded in the signal received over telecommunications link 302 from computer 24. Upon selecting the cooperating preform, computer 300 instructs robot mechanism 306 to extract that preform from magazine 304 (step 332, FIG.

19). In an inquiry 334, computer 300 checks whether the selected cooperating preform requires cutting to produce the required mold surface. If cutting is required, computer 300 controls robot mechanism 306 and cutting device 308 to perform the necessary cutting operations on the cooperating preform (step 336). In a subsequent step 338, computer 300 activates robot mechanism 306 to select another mold holder or support 312 and to attach the machined cooperating preform thereto.

Upon the positioning of the machined preforms or mold components in mold holders 310 and 312, robot mechanism 316 acts under the control of computer 300 to place the mold holders 310 and 312 and attached mold components into an apparatus 314 for introducing a quantity of a fluidic solidifiable dental material into the mold cavity defined by the two mold preforms or components. Apparatus 314 exemplarily takes the form of an injection molding machine, a casting machine or an injection press (see FIG. 26). Apparatus 314 includes a reservoir or store 316 of the fluidic solidifiable dental material which may be a metal or metal alloy or other dental composition. In a step 340, computer 300 operates apparatus 314, for example, through a valve 318, to introduce the fluidic dental material, e.g., molten metal, into the mold cavity. A collector 319 is provided for catching excess metal. The excess metal is then returned to reservoir 316.

Figure 20:
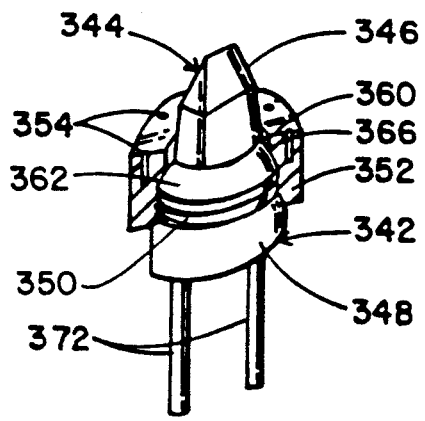
FIG. 20 is a perspective view, partially in cross-section, of a mold component usable in the system of FIG. 18 for forming a metal substructure portion of a crown.
Figure 21:
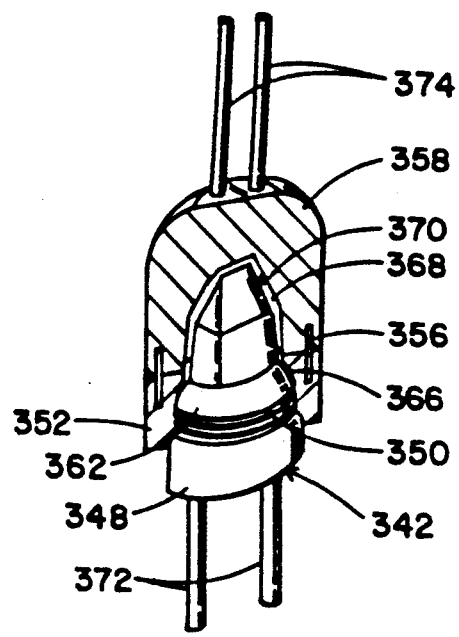
FIG. 21 is a perspective view, partially in cross-section, of the mold component of FIG. 20 in juxtaposition with another mold component, thereby forming a mold cavity for casting, injection molding or press molding a crown.
Figure 22:
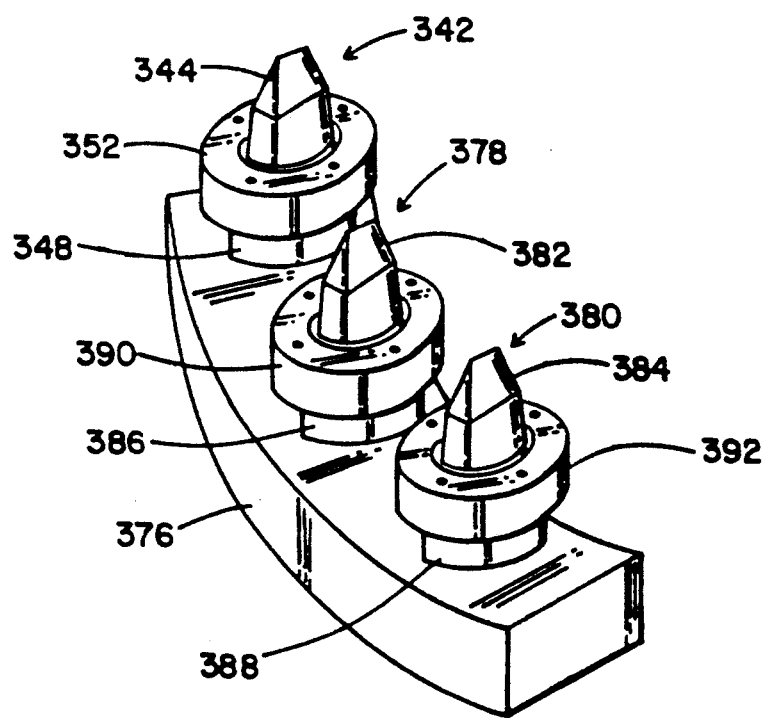
FIG. 22 is a perspective view of a plurality of mold components substantially similar to the mold component of FIG. 20, all attached to a mold holder or support in accordance with the present invention.

As depicted in FIGS. 20, 21 and 22, a mold preform or component 342 has a body 344 with a surface 346 corresponding to the surface of a dental preparation (either actual or planned) as specified in the signal arriving at computer 300 over telecommunications link 302 from computer 24. Body 344 of mold preform 342 is provided with a base portion 348 in turn provided with an external screw thread 350 which meshes with an internal screw thread (not separately designated) of an annular mold part or ring 352.

Ring 352 is provided with plurality of circumferentially spaced, axially extending bores 354 for receiving respective connector or guide pins 356 extending from another mold preform or component 358. Ring 352 is also provided with an inner surface 360 which is machinable to provide a close tolerance in cooperating with a corresponding surface 362 of mold component 342 to form a skirt portion 366 of a mold cavity 368. Skirt portion 366 of mold cavity 368 produces a gingival skirt extension (not shown) of a cast dental prosthesis substructure (not shown). Because the gingival skirt extension may extend to fit between the tooth and the gum of the patient, it is necessary that the extension be made very thin and is produced with a strict or narrow tolerance.

Mold component 358 has an inner surface 370 corresponding to an outer surface (opposite the prepared tooth surface) of a metallic portion of a respective dental prosthesis substructure. Surface 370 cooperates with surfaces 346 and 360 to define mold cavity 368.

As described hereinabove with reference to FIGS. 18 and 19, mold components 342 and 358 are machinable, particularly on surfaces 346 and 370, to provide mold cavity 368 with the precise surfaces, dimensions and configuration requested by the dental practitioner in the signal transmitted from computer 24 to computer 300 over link 302 (FIG. 18). Although ring 352 may be incorporated as a unitary or integral part of mold component 342, under certain conditions where marginal requirements are not easily machined, it is advantageous to provide the ring as a separate component to facilitate the machining of surface 360.

It is to be noted that the machining operation, carried out, for example, by cutting device 308 in FIG. 18, may be accomplished by any of a number of well known methods. Such methods include drilling, laser etching, ultrasonic material removal and electroerosion.

It is to be further noted that the machining operations are carried out on the preforms or mold components 342 and 358, rather than on a cast metallic blank. This results in a reduction in machining times and costs since great numbers of mold blanks of various geometries can be kept in stock, enabling a very close fit selection of the desired part number to be used. Pursuant to the invention, little of no machining of the finished metal casting, coping, crown, inlay or other product is required, thereby maintaining the integrity of the piece and minimizing if not eliminating the introduction of stress points and fatigue or gaseous elements locked into the metal substructure product. As discussed hereinafter, the use of the method in accordance with the invention to produce multiple tooth prostheses such as bridges will also contribute to the strength and longevity of those dental appliances by eliminating gaseous elements inherent in castings, and by eliminating the necessity for soldering, which naturally introduces stresses into the bridge material.

As shown in FIGS. 20 and 21, mold components 342 and 358 are provided with elongate rods or pins 372 and 374 for releasably attaching the mold components to respective mold supports, e.g., mold holder 376 in FIG. 22. As shown in that drawing figure, mold holder 376 carries a plurality of mold components 342, 378 and 380 each including a respective body portion 344, 382 and 384, base portion 348, 386 and 388, and ring or flange 352, 390 and 392. Mold components 342, 378 and 380 are spaced from one another and correspond to different teeth, possibly of different patients, perhaps even patients of different dental practitioners. Computer 300 (FIG. 18) is programmed to place several mold components such as component 342 or 358 on the same mold holder to thereby provide for the production of several dental prosthesis substructures simultaneously.

Figure 23:
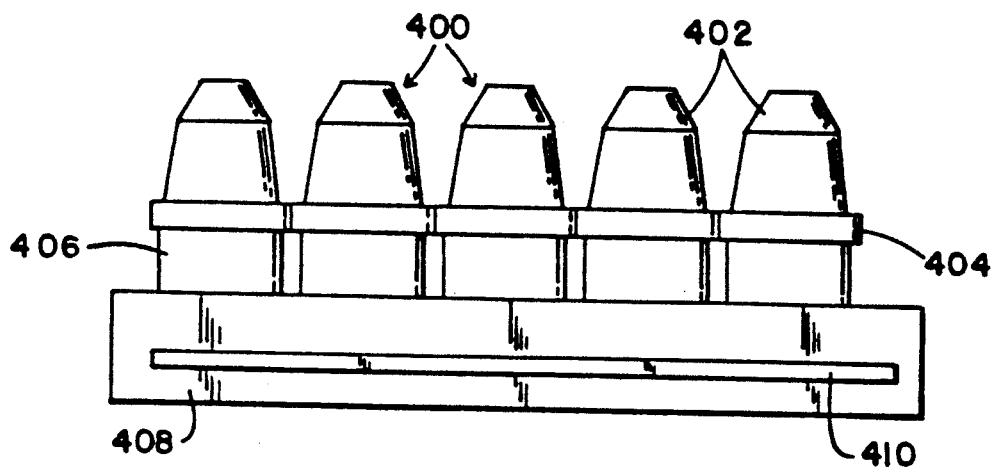
FIG. 23 is a diagrammatic side elevational view of a mold support carrying a plurality of inner mold components corresponding to respective adjacent teeth in the mouth of a single patient.

Alternatively, if required by a particular patient's dental condition, a bridge or splint can be produced using the techniques described herein. As illustrated in FIG. 23, a plurality of mold components 400 having body portions 402, gingival rings or flanges 404 and base portions 406 are connected in an arcuate array (not visible in diagrammatic illustration of FIG. 23) to a mold holder or support member 408. Mold holder 408 is provided with releasable attachment elements such as grooves or ribs 410 for facilitating the attachment of the mold holders to a molding machine (see FIG. 26 and the accompanying description). Body portions 402 of mold components 400 have surfaces which match the surfaces of respective tooth preparations actual or planned) such as full crown forms shaped as posts to which a patient's teeth have been reduced or are to be reduced.

Figure 24:
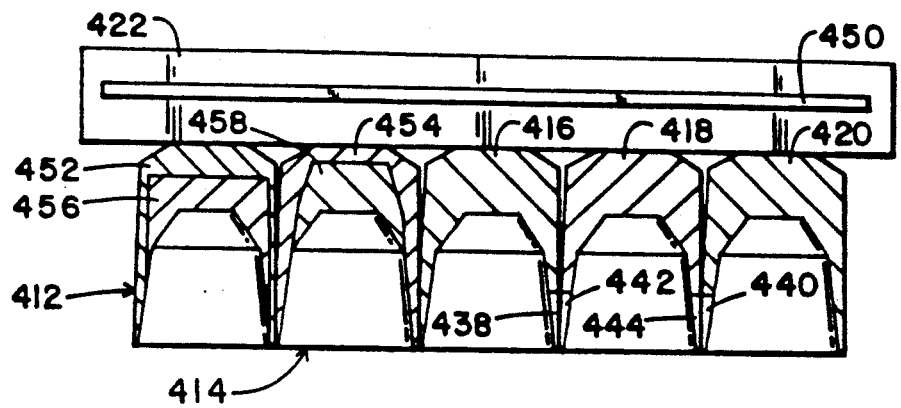
FIG. 24 is diagrammatic side elevational view of a mold support carrying a plurality of outer mold components corresponding to the inner mold components of FIG. 23.
Figure 25:
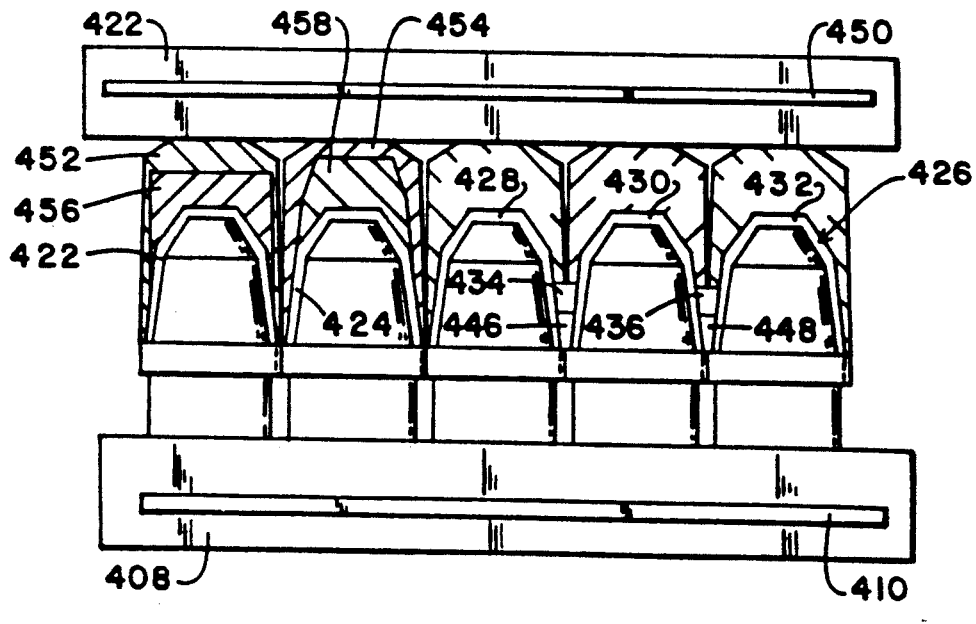
FIG. 25 is a diagrammatic side elevational view of the mold supports and inner and outer mold components of FIGS. 23 and 24, showing the mold components disposed in fitted juxtaposition to one another to form a plurality of mold cavities for forming the metal or allow substructures of a pair of crowns and a bridge.

As depicted in FIG. 24, a plurality of mold components 412, 414, 416, 418 and 420 for forming the outer surfaces (non-tooth-contacting surfaces) of dental prostheses for a single patient's mouth are secured to a mold holder or support 422 in an arcuate array matching the array of FIG. 23. As depicted in FIGS. 23 and 24, mold components 400 are inner or male mold components, while components 412, 414, 416, 418 and 420 are outer or female mold components. The inner mold components 400 are at least partially inserted into respective ones of the outer mold components 412, 414, 416, 418 and 420, as shown in FIG. 25, to form a plurality of mold cavities 422, 424 and 426. Mold cavities 422 and 424 correspond to individual teeth, i.e., form the metal portions of respective crowns, while mold cavity 426 comprises three crown-shaped spaces 428, 430 and 432 connected by bridging spaces 434 and 436 to form a bridge prosthesis, wherein units are attached or splinted to each other.

As illustrated in FIG. 24, mold components 416 and 420 are each provided in a side wall with a respective slot 438 and 440, while mold component 418 is provided in opposite side walls with a pair of slots 442 and 444 essentially coextensive with slots 438 and 440, respectively. After the automatic insertion of inner mold components 400 into outer mold components 412, 414, 416, 418 and 420, a first wedge 446 is automatically inserted into communicating slots 438 and 442 and a second wedge 448 is inserted into communicating slots 440 and 444, thereby defining bridging spaces 434 and 436.

Figure 26:
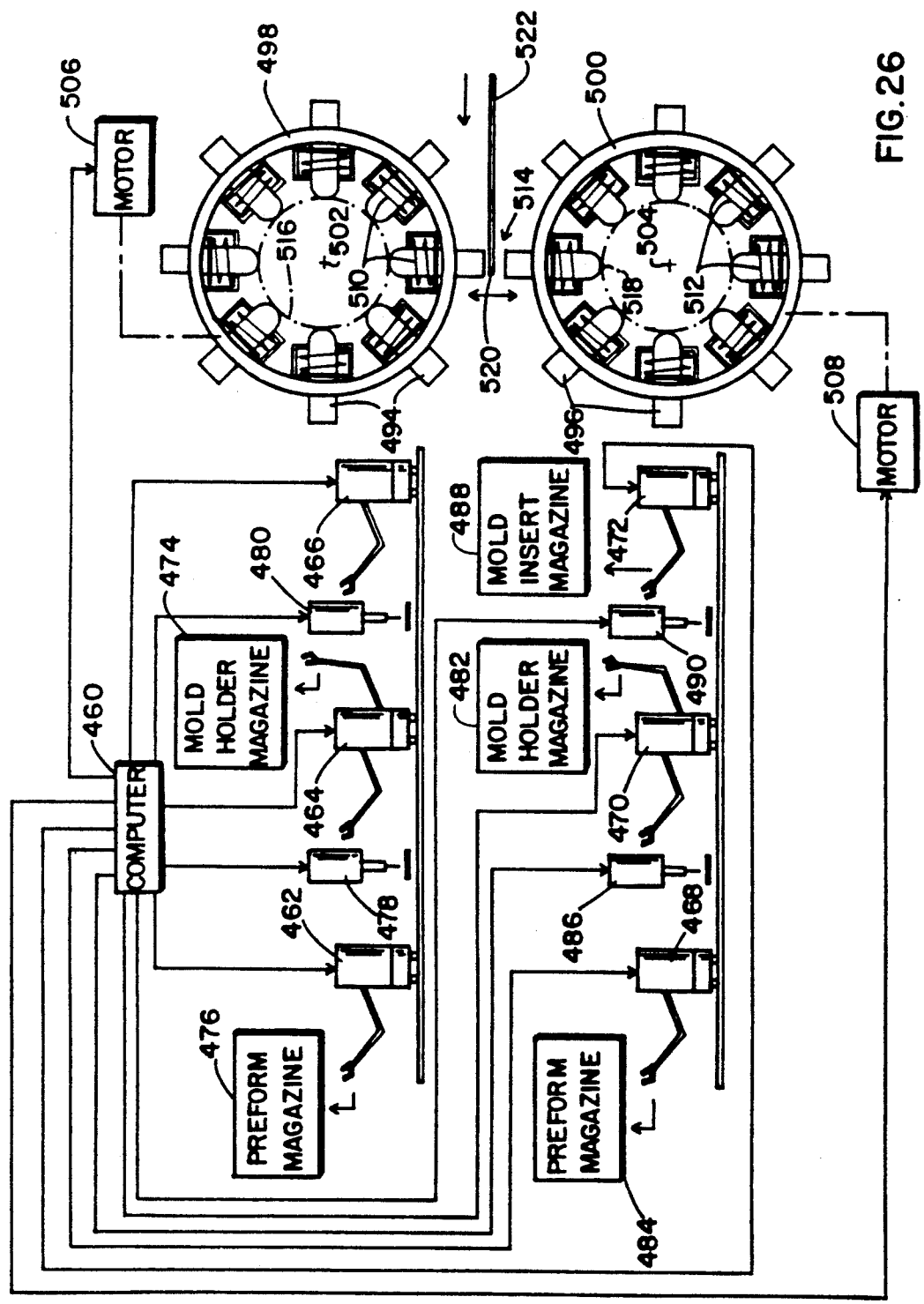
FIG. 26 is a diagram of another system for manufacturing a dental prosthesis, in accordance with the present invention, particularly for manufacturing a metal or alloy substructure of the prosthesis.

Mold holder or support member 422 is provided with at least one attachment member such as a groove or rib 450 for facilitating the attachment of the mold holders to a molding machine (see FIG. 26 and the accompanying description).

As further illustrated in FIGS. 24 and 25, outer mold components 412 and 414 comprise respective outer mold parts 452 and 454 into which inserts 456 and 45 have been placed for adapting mold parts 452 and 454 to conform to the electrically encoded three-dimensional surface of the respective dental prosthesis substructure, as transmitted from computer 24 to computer 300 over link 302 (FIG. 18). The inserts are obtained from a store or magazine of mold inserts and may be machined as described herein to conform the operative surfaces of the inserts to the three-dimensional data received from dental practitioners.

A mold assembly as shown in FIGS. 23 and 24, made in accordance with the invention, may be retained as a separate inventory piece or stock item subsequently to the use thereof. A manufacturing facility operating pursuant to the methods described herein builds its inventory of mold components and mold assemblies (i.e., bridges, splints and other multiple tooth type mold units) by accumulating the used mold components and mold assemblies. Computer 300 controls the arrangement and rearrangement of the stock items and continually updates its memory registry thereof.

As illustrated in FIG. 26, another system for manufacturing dental prosthesis substructures comprises a remote computer 460, analogous to computer 300 in FIG. 18 and connectable via telecommunications link 302 to a multiplicity of local computers such as computer 24 in FIG. 1. Computer 460 is operatively connected to a plurality of robot mechanisms 462, 464, and 466 for forming a first mold assembly, for example, the inner mold component assembly of FIGS. 23 and 25. Computer 460 is also operatively connected to another plurality of robot mechanisms 468, 470, and 472 for forming a second mold assembly, for example, the outer mold component assembly of FIGS. 24 and 25, which cooperates with the first mold assembly to form a plurality of dental mold cavities or chambers.

Upon receiving a signal identifying a substructure for a complex three-dimensional dental prosthesis such as a bridge, computer 460 scans its internal memory banks for a mold component assembly having at least two mold components closely corresponding in three-dimensional surface configuration to respective tooth preparation surfaces of the requested bridge. Upon selecting such a mold assembly, computer 460 activates robot mechanism 464 to retrieve the selected mold assembly from an inventory magazine 474 of mold holders including previously made mold assemblies such as that shown in FIG. 23.

As described hereinabove with reference to FIGS. 18 and 19, computer 460 then selects from its memory banks one or more mold components for teeth not having a corresponding mold component on the selected mold assembly. Computer 460 operates robot mechanism 462 to retrieve the selected mold components from a preform magazine 476 and to place the selected components in a cutting or machining device 478. Machining device 478 is operated under the control of computer 460 to conform the operative surfaces of the selected mold components to the respective electrically encoded three-dimensional surface data of the tooth preparations. In response to signals received from computer 460, robot mechanism 464 removes the finished mold component or components from machining device 478 and places them in proper positions on the selected mold assmbly unit.

Alternatively, if a suitable previously manufactured mold assembly is not available in the inventory of the manufacturing facility, computer 460 operates robot mechanisms 462 and 464 to prepare a new assembly from the basic stock mold components. In that event, a blank mold holder (not illustrated) is obtained by robot mechanism 464 from magazine 474. Under the control of signals from computer 460, robot mechanism 464 and another machining device 480 drills holes in the mold holder in relative locations corresponding to the array of tooth preparations for the bridge. The mold holder is provided with two bores for each mold component or preform obtained by robot mechanism 462 from preform magazine 476, the bores determining the position and orientation of the respective mold component in the array. The position and orientation of the mold component in the array is based on analysis and computation of the original surface data digitized into the system.

While robot mechanisms 462 and 464 are working on a mold assembly of inner mold components (see FIGS. 23 and 25), computer 460 controls robot mechanisms 468 and 470 to assemble a mold component assembly of outer mold components (see FIGS. 24 and 25). If a suitable previously manufactured mold assembly exists in a mold assembly and mold holder magazine 482, robot mechanism 470 retrieves the mold assembly pursuant to signals from computer 460. Also under the control of computer 460, robot mechanism 468 retrieves additional or replacement mold components from a preform magazine 484 and positions them in a machining apparatus 486 which cuts the preforms or mold components to the specifications obtained from the dental practitioner as described above. In the event that one or more outer mold components (see reference designations 412 and 414 in FIGS. 24 and 25) require inserts to adapt them to the specification from the practitioner, computer 460 commands robot mechanism 472 to retrieve appropriate mold inserts (e.g., inserts 456 and 458 in FIGS. 24 and 25) from a store or magazine 488 of mold inserts. In response to signals from the computer, robot mechanism 472 and an additional machining apparatus 490 cooperate to machine the inserts to the prosthesis specifications from the dental practitioner.

Upon the assembly of the outer mold components and the inserts by robot mechanisms 470 and 472, computer 460 controls one or the other robot mechanism to obtain wedges (e.g., 446 and 448 in FIG. 25) for insertion between adjacent mold components in the bridge mold assembly. The wedges are obtained from an inventory in a magazine (not shown) and may be machined for exact fit within close tolerance ranges.

Upon the completion of the inner and outer mold component assemblies, robot mechanisms 466 and 472 attached the mold assemblies to respective piston or plunger members 494 and 496 which are reciprocatingly mounted to respective drums 498 and 500. Drums 498 and 500 are step-wise rotated about respective axes 502 and 504 by motors 506 and 508 energized under the control of computer 460.

Each plunger member 494 and 496 is biased towards a radially inward position by a respective tension spring 510 and 512 (compression springs may be used instead). When the plunger members 494 and 496 reach a nip 514 between the two drums 498 and 500, the plungers members are pushed towards one another, for example, by camming surfaces 516 or 518 or any other technique (such as pneumatic cylinders, not shown).

During the insertion of the inner mold components into the respective outer mold components occasioned by the pushing of plunger members 494 and 496 towards one another, a free end 520 of a continually advancing ribbon 522 of fluidic solidifiable dental material such as a precious metal or alloy in a hot semisolid form is sheared off and assumes the form of the mold cavity or cavities defined by the inner and outer mold components diposed in the juxtaposed plunger members 494 and 496. Upon a subsequent rotation of drums 498 and 500 by motor drives 506 and 508 under the control of computer 460, the mold components are separated from one another and the molded dental prosthesis substructure thereby made available for removal and shipment to the dental practitioner who ordered the prosthesis substructure. A layer of porcelain or other cosmetic covering may be applied to the outer surface of the dental prosthesis substructure prior to shipment.

In an alternative manufacturing scenario, a portion of the above-described manufacturing steps are performed at one location by one party, while other steps are performed at another location by another party. Specifically, a supplier of dental compositions such as precious metals and alloys is equipped with an inventory of mold components, mold inserts and mold supports for producing nearest net shapes or blanks. In response to an order from a dental laboratory for a substructure of particular type of dental prosthesis (crown, bridge, etc.) having specified dimensions and surfaces as described hereinabove, the supplier sends to the laboratory a blank of precious metal or alloy having dimensions slightly larger than the dimensions of the ordered prosthesis substructure. In addition, the supplier might send mold components for producing from the blank the ordered prosthesis substructure in accordance with the methods described hereinabove with reference to FIGS. 18, 19 and/or 26. In that event, the supplier also transmits to the dental laboratory, for example, on a floppy disk or other electronic storage medium accompanying the blank and the mold components, an electrical signal encoding the three-dimensional surface characteristics of the mold components.

The dental laboratory, upon receiving the slightly oversized nearest net shape or blank from the supplier, prepares the mold components for press molding the desired prosthesis substructure from the blank. This preparation entails minor machining of the mold components, if necessary, as described hereinabove. The prepared mold components, together with the oversized nearest net shape or blank, are placed in an oven and heated to a predetermined press molding temperature appropriate to reduce the material of the precious metal or alloy or other solidifiable dental composition to a fluidic semisolid state capable of fluid flow under pressure. Then the mold components are pressed together, with the dental substructure blank inserted therebetween, to apply a compressive pressure to the blank to eliminate inaccuracies in the blank's shape. Any excess metal or alloy, which will be limited to a small amount, is squeezed from between the mold components during the press molding process and may be sliced off and collected for return to the supplier.

Upon a subsequent cooling of the molded prosthesis substructure, a porcelain layer is applied to an outer surface of the substructure by techniques similar to those described above with respect to the manufacture of the substructure. The laboratory prepares the procelain layer in accordance with an specifications encoded in the electrical signal which it has received from a dental practitioner as part of an order for the completed dental prosthesis. In particular, the dental laboratory removes the outer or female mold component(s) from the press molded prosthesis substructure(s), while retaining that substructure(s) on the inner or male mold component(s). A cavity or space formed by another outer or female mold component is then filled with a fluidic porcelain composition. This other outer or female mold component has an inwardly facing surface which conforms to the outer surface of the porcelain layer of the dental prosthesis, as specified in the order placed by the dental practitioner. Upon an introduction of the fluidic porcelain material into the outer mold component, the original inner mold component holding the press molded prosthesis substructure and the new outer mold component holding the fluidic porcelain material are moved into mating juxtaposition with one another so as to press the fluidic porcelain material to the outer surface of the press molded prosthesis substructure. This process is carried out at temperatures suitable to the maintenance of a suitable viscosity to the fluidic porcelain material.

Figure 27:
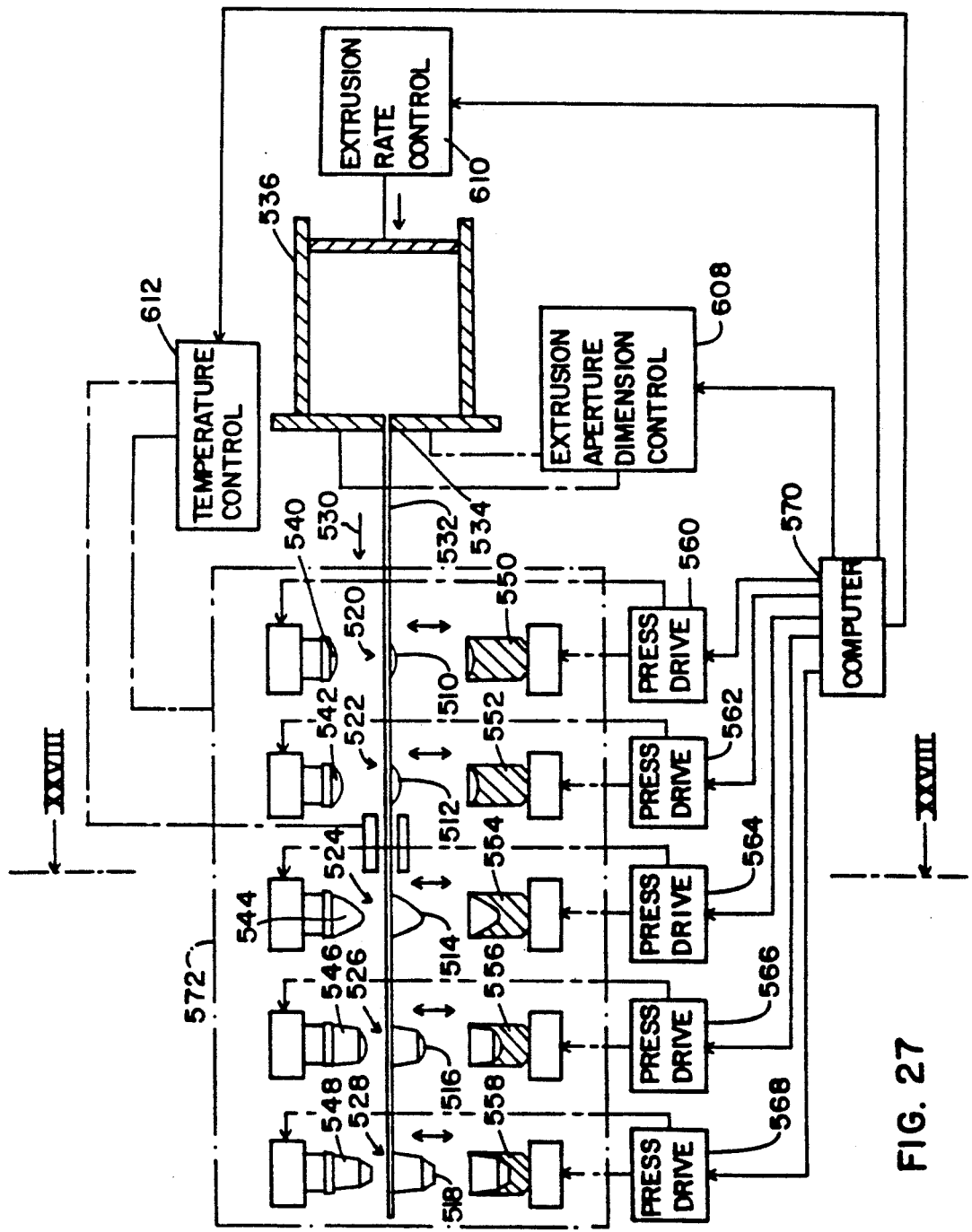
FIG. 27 is a diagrammatic representation of yet another system for manufacturing a dental prosthesis, in accordance with the present invention, particularly for manufacturing a metal or alloy substructure of the prosthesis.
Figure 28:
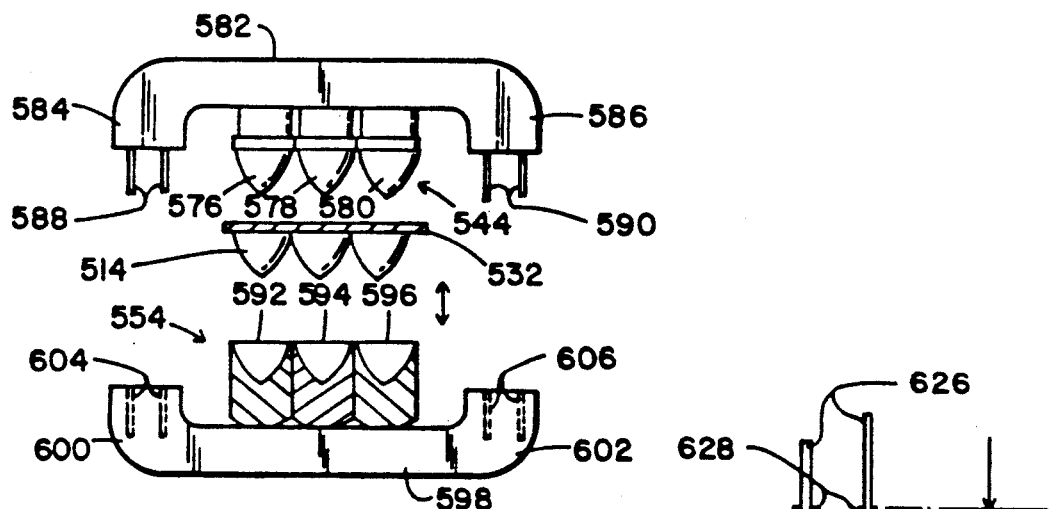
FIG. 28 is a view taken along line XXVIII—XXVIII in FIG. 27.

As shown in FIGS. 27 and 28, a metal substructure of a dental prosthesis such as a three-unit bridge or splint is advantageously fabricated through an incremental press molding process in which successive approximations 510, 512, 514, 516, 518 of the final product are pressed at a series of press molding stations 520, 522, 524, 526, and 528 spaced along a feed path or direction 530 of a continuously cast or extruded ribbon or strip 532 of precious metal, alloy or other maleable and deformable dental material. Ribbon 532 emerges from an aperture 534 of a continuous casting or extrusion machine 536 where the deformable dental material is maintained in a fluidic state by elevated temperatures and pressures.

At each molding station 520, 522, 524, 526, and 528, a respective male or inner mold component 540, 542, 544, 546 and 548 is pressed towards and partially into a respective female or outer mold component 550, 552, 554, 556 and 558 by a respective drive mechanism 560, 562, 564, 566 and 568 controlled by a computer 570 analogous to computer 300 in FIG. 18 and connectable via telecommunications link 302 to a multiplicity of local computers such as computer 24 in FIG. 1, Drive 560 is operated first to form dental substructure approximation 510 from ribbon or strip 532. Ribbon 532 then advances to station 522 where drive mechanism 562 presses male or inner mold component 542 into female or outer mold component 552 to form approximation 512. approximations 514, 516, and 518 are formed at successively later times at respective stations 524, 526, and 528.

As indicated schematically by a dot-dash line, the successive approximation press molding procedure may take place in an oven chamber 572 at suitably elevated temperatures. Additionally or alternatively, ribbon or strip 532 may be maintained at elevated temperatures by a plurality of heater devices 574 (only one shown in the drawing) disposed along the path of ribbon 532 between stations 520, 522, 524, 526, and 528.

A successive approximation process in accordance with the invention facilitates the production of the finished dental prosthesis substructures and results in a superior product owing the the continual annealing of the dental material during the process and particularly between successive press molding operations.

As illustrated particularly in FIG. 28, male or inner mold component 544 (like the other male or inner mold components 540, 542, 546 and 548) includes a plurality of male mold elements 576, 578 and 580 mounted in an appropriately arced array to a mold support or holder member 582 formed at opposite ends with a pair of arms 584 and 586 in turn provided at their ends with guide pins 588 and 590. Similarly, female or outer mold component 554 (like the other female or outer mold components 550, 552, 556 and 558) includes a plurality of female mold elements 592, 594 and 596 mounted in a similarly arced array to a mold support or holder member 598 provided at opposite ends with a pair of arms 600 and 602 in turn provided at their ends with bores 604 and 606 for receiving guide pins 588 and 590 during a mold closing motion.

Upon receiving from computer 24 (FIG. 1) electrical signals encoding the three-dimensional surface characteristics of a bridge, computer 570 selects male or inner mold components 540, 542, 544, 546 and 548 and female or outer mold components 550, 552, 554, 556 and 558 from an inventory of such mold component, as described hereinabove. Such mold components may be machined, if necessary. In addition, one or more of the female or outer mold components 550, 552, 554, 556 and 558 may comprise an outer mold body and an insert or nest element, as described in detail above with reference to FIGS. 24 and 25.

Upon selecting the male or inner mold components 540, 542, 544, 546 and 548 and the female or outer mold components 550, 552, 554, 556 and 558, computer controls the disposition thereof by robot mechanisms (not shown in FIGS. 27 and 28) at press mold stations 520, 522, 524, 526, and 528, as described hereinabove with reference to FIG. 26. Press mold stations 520, 522, 524, 526, and 528 may particularly take the form of respective pairs of drums with slidably mounted pressure members, as described in detail above with reference to FIG. 6. Other possible press mold realizations within the contemplation of the invention include conventional hydraulic and pneumatic mechanisms controllable by computer 570.

Computer 570 is capable of overseeing the manufacture of several dental prosthesis substructures simultaneously. Thus, ribbon 532 may be formed along its length with a continuous sequence of approximating forms for different dental prostheses. Because each prosthesis comprises a unique combination of dental forms and a substructure having a specific unique volume, the amount of material required, as well as molding temperatures and the number of requisite approximations will vary from prosthesis to prosthesis. Based on the digitized surface information included in the electrical signals arriving from practitioners, either directly or through dental laboratories, computer 570 is accordingly programmed to calculate and implement variations in such processing parameters as the thickness of ribbon 532 and the temperature thereof, as well an the number and degree of the successive approximations for each individual prosthesis. Computer 570 generates signals transmitted to a device 608 for instantaneously controlling the height and/or width of extrusion aperture 534 to accord with the material requisites of the series of prosthetic substructures. The rate at which ribbon 532 advances is also controlled by computer 570 through an extrusion rate control device 610. Temperatures of ribbon 532 along its length are controlled by computer 570 via a temperature control device 612.

As described above, a prefinal approximation (e.g., approximation 518), together with mold components both for the load bearing substructure and for any surface layer (e.g., porcelain), may be conveyed to a dental laboratory for final operations to produce the complete, finished product.

Figure 29:
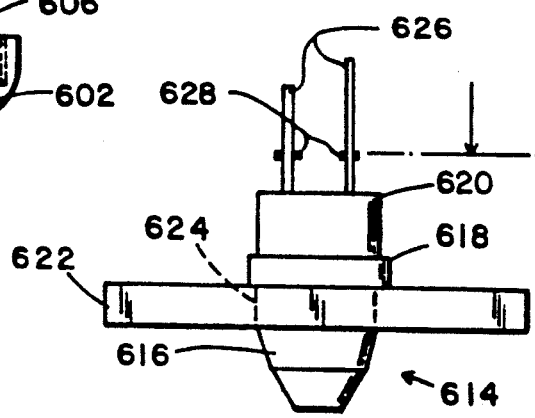
FIG. 29 is a schematic side elevational view of a preformed mold component in a magazine or storage rack, in accordance with the present invention.

As shown in FIG. 29, a male or inner mold component 614 including a body portion 616 with a surface conforming to a dental preparation, a gingival ring structure 618 and a base or stem portion 620 is stored on a magazine rack 622 accessible by a robot mechanism in accordance with the invention. Body portion 616 extends through an aperture 624 in rack 622, while ring structure 618 rests thereon. Base or stem 620 carries a pair of locating pins or fingers 626, each provided with at least one projection 628 in the form of a nub or rib. All male and female mold components described herein are provided such locating pins or fingers and indexing projections to facilitate automatic handing of the mold components by the robot mechanisms. During an automatic selection procedure in accordance with the invention, a robot mechanism (not shown in FIG. 29) grasps mold component 614 by sliding a gripping mechanism downwardly over pins 626 until projections 628 are encountered. The robot then locks the mold component into place and proceeds with manipulating the mold component in the steps described above.

Figure 30:
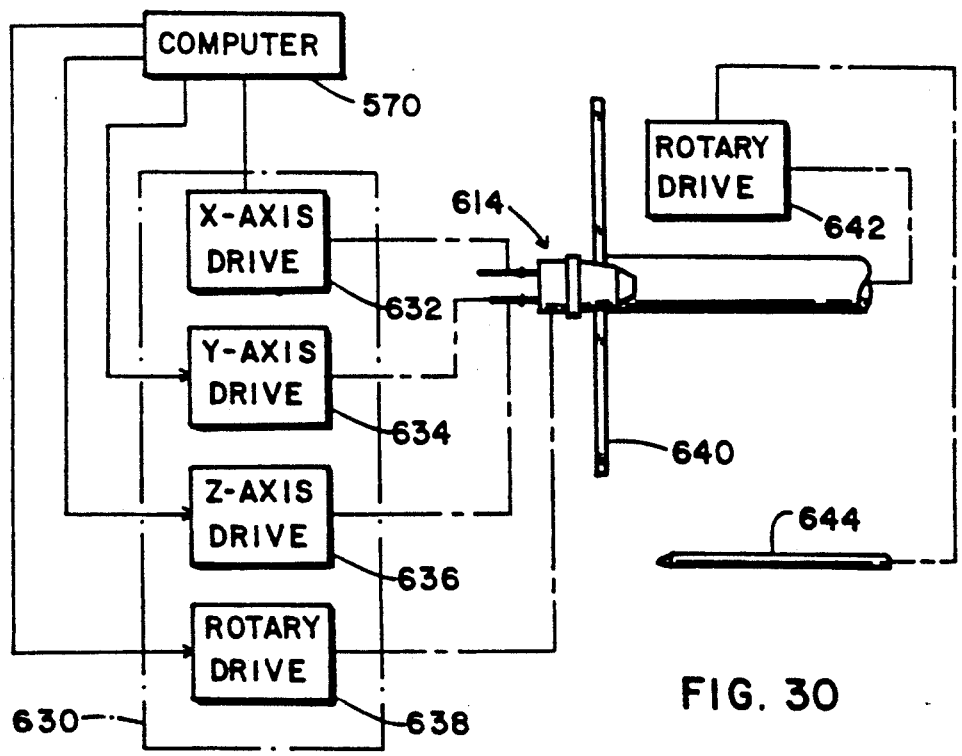
FIG. 30 is a diagrammatic representation of a portion of a system for manufacturing a dental prosthesis in accordance with the present invention.

As depicted in FIG. 30, upon the grasping of mold component 614 by a robot mechanism 630, a computer such as computer 570 in FIG. 27 transmits signals to x-axis drive 632, y-axis drive 634, z-axis drive 636 and/or a rotary drive 638 to control the formation of desired surface characteristics on body portion 616 and in ring structure 618. Through robot mechanism 630, computer 570 controls the extent and nature of material-removing machining on body portion 616 by an abrasive disk 640 rotated at high speed by a drive 642 about an axis extending generally parallel to the axis of mold component workpiece 614. Further features, including the size of a groove formed in gingival ring 618 and surface indentations not formable via disk 640, are machined via a point-milling drill, ultrasonic wave generator or laser tool 644. Numerical control of the mold component workpiece 614 relative to machine tools 640 and 644 is maintained at all times by computer 570.

Upon the completion of machining as illustrated in FIG. 30, a second robot mechanism (not shown in FIG. 30) grasps the mold component 614 by its body portion 616 and places the mol component in a mold holder or support (e.g., 582, 598, FIG. 30) in which the holes for receiving locating pins 626 have already been formed.

It is to be noted that holes or bores formed in a mold component holder or support (see, e.g., reference designations 582 and 598) for receiving locating pins (e.g., 626) have an orientation and depth determined in accordance with the incoming three-dimensional surface information. Even in the event that the prosthetic device is only a crown, the information provided by the dental practitioner includes the relative positions of adjacent teeth and of the opposite tooth forming the bite. The control computer 300, 460 or 570 takes that information into account in determining the angle that a mold component is placed into the respective mold holder prior to a casting or press molding operation as described herein.

An enormous advantage of a system and method in accordance with the invention for producing a dental prosthesis is that milling or machining is minimized and is almost entirely confined to the mold components. The actual substructure and finished product requires little or no machining. Accordingly, accuracies are enhanced over conventional CAD/CAM processes which produce a dental prosthesis by milling from a block-shaped blank.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A method for use in preparing a dental prosthesis, comprising the steps of:
   providing an electrical signal encoding geometric specifications of a substructure of the prosthesis, said specifications including dimensions and shape of a tooth preparation at a dental site at which the prosthesis is to be affixed and configuration of said substructure;
   in response to said electrical signal, providing a first mold component having a surface at least approximately conforming to said tooth preparation and a second mold component to produce, in cooperation with said first mold component, a mold cavity having dimensions and configuration corresponding at least substantially to dimensions and configuration of said substructure;
   placing said first mold component and said second mold component in predetermined relative positions to form said mold cavity;
   introducing into said mold cavity a quantity of a fluidic solidifiable dental material; and
   removing a prosthesis substructure form from said mold cavity upon solidification of the dental material with which said mold cavity is filled.

2. The method defined in claim 1 wherein said step of introducing comprises the step of filling one of said first mold component and said second mold component with said fluidic solidifiable dental material prior to said step of placing, said step of placing comprising the step of at least partially inserting the other of said first mold component and said second mold component into said one of said first mold component and said second mold component.

3. The method defined in claim 1 wherein said fluidic solidifiable dental material comprises a semisolid deformable mass, said step of placing comprising the steps of positioning said first mold component and said second mold component on opposite sides of deformable mass and subsequently moving said first mold component and said second mold component towards one another, said step of introducing comprising the step of shearing off a portion of said deformable mass by said first mold component and said second mold component during said step of moving.

4. The method defined in claim 1 wherein said fluidic solidifiable dental material takes the form of a molded blank, said step of placing comprising the steps of positioning said first mold component, said second mold component and said blank so that said first mold component and said second mold component are disposed on opposite sides of said blank and subsequently moving said first mold component and said second mold component towards one another, said step of introducing comprising the step of seating said blank into said mold cavity during said step of moving.

5. The method defined in claim 4 wherein said blank has a shape substantially conforming to said specifications.

6. The method defined in claim 1 wherein said step of providing includes the step of operating a computer to select said first mold component and said second mold component from a plurality of mold preforms in accordance with said specifications.

7. The method defined in claim 1 wherein said step of introducing is performed subsequently to said step of placing.

8. The method defined in claim 7 wherein said step of introducing includes a step of injecting said fluidic solidifiable dental material into said mold cavity upon formation thereof during said step of placing.

9. The method defined in claim 1 wherein said step of introducing is performed in part during said step of placing.

10. The method defined in claim 9 wherein said step of introducing comprises the steps of pouring said fluidic solidifiable dental material into a mold form including one of said first mold component and said second mold component and subsequently shifting the other of said first mold component and said second mold component relatively towards said one of said first mold component and said second mold component to form said mold cavity filled with said fluidic solidifiable dental material.

11. The method defined in claim 1, further comprising the step of selectively removing material from said first mold component prior to said step of placing.

12. The method defined in claim 11 wherein said step of selectively removing is performed automatically in response to said electrical signal.

13. The method defined in claim 11 wherein said step of selectively removing comprises at least one of electro-eroding and ultrasonically treating the material of said first mold component.

14. The method defined in claim 1, further comprising the step of selectively removing material from said second mold component prior to said step of placing.

15. The method defined in claim 14 wherein said step of selectively removing is performed automatically in response to said electrical signal.

16. The method defined in claim 14 wherein said step of selectively removing comprises at least one of electro-eroding and ultrasonically treating the material of said second mold component.

17. The method defined in claim 1 wherein said steps of placing and introducing are performed automatically.

18. The method defined in claim 17 wherein said steps of placing and introducing comprise the steps of operating a computer to control a robotic device to (a) place said first mold component and said second mold component in relative positions to form said mold cavity and (b) introduce into said mold cavity a quantity of a fluidic solidifiable dental material, said computer selecting said relative positions in accordance with information included in said electrical signal defining said relative positions based on a patient's dentition.

19. The method defined in claim 1 wherein said step of placing comprises the steps of attaching said first mold component and said second mold component to respective mold supports and then positioning said mold supports relative to one another.

20. The method defined in claim 19 wherein one of said mold supports comprises a plate member provided with an array of predetermined positions for receiving said first mold component, the other of said mold supports comprising a plate member provided with an array of positions for receiving said second mold component, said positions being determined in part in accordance with information obtained from a scan of a patient's dentition.

21. The method defined in claim 19 wherein said first mold component and said second mold component are each provided with a pin insertable into apertures in the respective mold support.

22. The method defined in claim 1 wherein said first mold component and said second mold component are provided with a plurality of mounting pins, further comprising the step of machining apertures for receiving said mounting pins in a pair of mold support members.

23. The method defined in claim 1 wherein said step of providing an electrical signal comprises the step of receiving said electrical signal.

24. The method defined in claim 23 wherein said electrical signal is transmitted via a telecommunications linkage.

25. The method defined in claim 23 wherein said electrical signal is communicated via a transported memory element.

26. The method defined in claim 25 wherein said memory element is a floppy disk.

27. The method defined in claim 1 wherein said fluidic solidifiable dental material is a deformable metallic composition.

28. The method defined in claim 1 wherein said fluidic solidifiable dental material is taken from the group including a deformable plastic substance, a glass material, a ceramic material, a composite glass and ceramic material.

29. The method defined in claim 1 wherein said second mold component includes a mold body and an insert.

30. The method defined in claim 29, further comprising the step of selectively removing material from said insert prior to said step of placing.

31. The method defined in claim 30 wherein said step of selectively removing is performed automatically in response to said electrical signal.

32. The method defined in claim 1 wherein said first mold component includes a mold body and an insert.

33. The method defined in claim 32, further comprising the step of selectively removing material from said insert prior to said step of placing.

34. The method defined in claim 33 wherein said step of selectively removing is performed automatically in response to said electrical signal.

35. The method defined in claim 1 wherein said tooth preparation takes a post-like form and wherein said first mold component includes a body with a base and a ring-shaped portion at said base.

36. The method defined in claim 35 wherein said ring-shaped portion is a separate piece attached to said body portion.

37. The method defined in claim 36, further comprising the step of selectively removing material from said ring-shaped portion along an inner surface thereof to form with said body a skirt region of said mold cavity.

38. The method defined in claim 1 wherein the prosthesis takes the form of an overlay.

39. The method defined in claim 38 wherein the prosthesis is a crown.

40. The method defined in claim 38 wherein the prosthesis is a bridge.

41. The method defined in claim 1, further comprising the steps of positioning a plurality of third mold components in a predetermined array determined in accordance with information contained in said electrical signal, positioning a plurality of fourth mold components in a corresponding array determined in accordance with information contained in said electrical signal, said first mold component constituting one of said third mold components, said second mold component constituting one of said fourth mold components.

42. The method defined in claim 41 wherein said steps of positioning comprise the steps of placing said third mold components in said predetermined array on a first mold support and of placing said fourth mold components in said corresponding array on a second mold support.

43. The method defined in claim 41 wherein said step of positioning a plurality of fourth mold components comprises the steps of selecting a mold support provided with a plurality of mold parts in said corresponding array, selecting at least one insert piece, and inserting said insert piece in one of said fourth mold components.

44. The method defined in claim 41, further comprising the step of selectively removing material from at least two of said fourth mold components to form a bridging portion between said two of said fourth mold components upon a filling of a mold cavity formed between said two of said fourth mold components and associated ones of said third mold components.

45. The method defined in claim 1, further comprising the steps of:
separating said second mold portion from said first mold portion and said prosthesis substructure form upon solidification of said fluidic solidifiable dental material and prior to said step of removing;

providing a third mold component having an inner surface substantially conforming to an outer surface of the prosthesis, as specified in said electrical signal;

placing said first mold component with the attached prosthesis substructure form and said third mold component in predetermined relative positions to form an additional mold cavity;

introducing into said mold cavity a quantity of another fluidic solidifiable dental material; and removing a substantially complete prosthesis form from said mold cavity upon solidification of the other fluidic solidifiable dental material with which said additional mold cavity is filled.

46. A system for use in preparing a dental prosthesis, comprising:

signal production means for producing an electrical signal encoding geometric specifications of a substructure of the prosthesis, said specifications including dimensions and shape of a tooth preparation at a dental site at which the prosthesis is to be affixed and configuration of the substructure;

robot means for placing a first mold component and a second mold component, selected in accordance with said electrical signal, in predetermined relative positions to form a mold cavity, said first mold component corresponding in shape and dimensions to said tooth preparation;

filling means for introducing into said mold cavity a quantity of a fluidic solidifiable dental material; and computing means operatively connected to said receiver means, said robot means and said filling means for controlling and sequencing the operation thereof in response to said electrical signal.

47. The system defined in claim 46, further comprising material removal means operatively connected to said computing means for selectively removing material, in response to signals from said omputing means, from at least one of said first mold component and said second mold component prior to placement of said second mold component into juxtaposition to said first mold component.

48. The ssytem defined in claim 47 wherein said material removal means includes means for removing material by at least one of electro-erosion and ultrasonic removal.

49. The system defined in claim 46 wherein said signal producing means includes receiver means for receiving said electrical signal and reproducing said signal for use by said computing means.

50. A method for manufacturing a customized dental rosthesis, comprising the steps of:

generating electrically encoded data representing a three-dimensional surface of a tooth to be restored, said step of generating including the steps of (a) tracing a contour of said three-dimensional surfaces with a stylus-type instrument provided with an extension disposed outside of he mouth in which said tooth is located and (b) optically monitoring movements of a predetermined point on said extension;

automatically feeding said data to a first computer;

operating said computer to generate an electrical signal encoding specifications of a substructure of the prosthesis, said specifications including dimensions of a tooth preparation at a dental site at which the prosthesis is to be affixed and configuration of the substructure; and transmitting said electrical signal to a second computer.

51. The method defined in claim 50 wherein said step of generating includes the step of optically scanning said three-dimensional surface.

52. The method defined in claim 51, further comprising the step of preparing said tooth to form said tooth preparation, said three-dimensional surface being a surface of said tooth preparation, said dimensions being actual dimensions of said tooth preparation.

53. The method defined in claim 51, further comprising the step of operating said first computer to calculate said dimensions, said dimensions being projected dimensions of said tooth preparation.

54. The method defined in claim 53 said step of operating said first computer to calculate includes the step of providing input to said first computer to designate dimensions and location of said tooth preparation.

55. The method defined in claim 54 wherein said step of providing input is implemented with a keyboard, 56. The method defined in claim 54 wherein said step of providing input is implemented with a mouse-type device.

57. The method defined in claim 50 wherein said step of operating said first computer to generate includes the step of computing a varying thickness dimension of said substructure so that a porcelain portion of the prosthesis has a substantially constant thickness throughout.

58. The method defined in claim 50 further comprising the step of operating said second computer to automatically control a robotic device to produce said substructure in response to said electrical signal.

59. The method defined in claim 58, further comprising the steps of controlling said robotic device via said second computer to (a) select a first mold component corresponding in dimensions to said tooth preparation, (b) select a second mold component to produce, in cooperation with said first mold component, a mold cavity having dimensions and configuration corresponding to dimensions and configuration of said substructure, (c) place said first mold component and said second mold component in predetermined relative positions to form said mold cavity and (d) fill said mold cavity with a quantity of a fluidic solidifiable dental material.

60. The method defined in claim 50 wherein said first computer and said second computer are disposed at respective locations remote from one another.

* * * * *